United States Patent [19]

Collins et al.

[11] Patent Number: 5,526,111
[45] Date of Patent: Jun. 11, 1996

[54] METHOD AND APPARATUS FOR CALCULATING A COAGULATION CHARACTERISTIC OF A SAMPLE OF BLOOD A BLOOD FRACTION OR A CONTROL

[75] Inventors: Rick L. Collins, Cicero; Martin T. Gerber, Carmel; Zindel H. Heller, Indianapolis; James L. Maxwell, Carmel, all of Ind.; Edna C. Probst, Cedar Rapids, Iowa; Loy M. Vail, Cicero, Ind.; Stefan Weinert, Fortville, Ind.; Morris J. Young, Indianapolis, Ind.

[73] Assignee: Boehringer Mannheim Corporation, Indianapolis, Ind.

[21] Appl. No.: 114,897

[22] Filed: Aug. 31, 1993

[51] Int. Cl.⁶ .......................... G01N 33/49; G06F 159/00
[52] U.S. Cl. .......................... 356/39; 73/64.43; 73/61.41; 73/53.01; 128/633; 128/635; 128/DIG. 22; 422/73; 436/69; 435/13
[58] Field of Search .......................... 364/413.07, 413.08, 364/413.09, 413.02, 413.01; 73/64.41, 64.43, 53.01, 61.41, 61.43; 422/73, 61; 356/39, 40, 41, 42; 324/621, 613, 635, 647; 128/632, 633, 668, 635, 637, DIG. 22; 210/645, 745; 436/69; 435/13

[56] References Cited

U.S. PATENT DOCUMENTS

| Re. 27,866 | 1/1974 | Adler | 23/253 R |
|---|---|---|---|
| Re. 28,009 | 5/1974 | Vicario | 73/64.1 |
| 3,593,568 | 7/1971 | Schmitz et al. | 73/64.43 |
| 3,635,678 | 1/1972 | Seitz et al. | 436/69 |
| 3,695,842 | 10/1972 | Mintz | 23/230 R |
| 3,699,437 | 10/1972 | Ur | 324/722 |
| 3,752,443 | 8/1973 | Lichtenstein | 366/274 |
| 3,754,866 | 8/1973 | Ritchie et al. | 422/73 |
| 3,821,643 | 6/1974 | Bostick et al. | 23/253 R |
| 3,833,864 | 9/1974 | Kiess et al. | 356/414 |
| 3,836,333 | 9/1974 | Mintz | 422/73 |
| 3,840,806 | 10/1974 | Stoner et al. | 324/722 |
| 3,967,934 | 7/1976 | Seitz et al. | 422/73 |
| 4,000,972 | 1/1977 | Braun et al. | 436/69 |
| 4,014,650 | 3/1977 | Sigelmann | 436/108 |
| 4,034,601 | 7/1977 | Geiger | 73/64.43 |
| 4,081,242 | 3/1978 | Girolami | 73/54.01 |
| 4,105,411 | 8/1978 | Biver | 422/73 |
| 4,112,740 | 9/1978 | Brandestini | 73/64.53 |
| 4,125,327 | 11/1978 | Margolis | 356/39 |
| 4,201,470 | 5/1980 | Ehrly et al. | 356/39 |
| 4,217,107 | 8/1980 | Saito et al. | 436/69 |
| 4,252,536 | 2/1981 | Kishimoto et al. | 356/36 |
| 4,388,823 | 6/1983 | Garnaud et al. | 73/54.18 |
| 4,400,353 | 8/1983 | Meserol et al. | 422/73 |
| 4,492,462 | 1/1985 | Pross et al. | 356/39 |
| 4,501,491 | 2/1985 | Breda et al. | 356/39 |

(List continued on next page.)

FOREIGN PATENT DOCUMENTS

| 0394041 | 10/1990 | European Pat. Off. |
| WO92/01065 | 1/1992 | WIPO |

Primary Examiner—Gail O. Hayes
Assistant Examiner—Joseph Thomas
Attorney, Agent, or Firm—Barnes & Thornburg

[57] ABSTRACT

A method for calculating a coagulation characteristic of a sample of blood, a blood fraction, or a control comprises generating an output signal indicative of coagulation of the sample, sampling the output signal at a sampling rate for a predetermined time to provide a plurality of sampled signal values, storing the sampled signal values, rectifying the stored sampled signal values to provide a plurality of envelope values, and storing the envelope values. The stored envelope values are examined in reverse time order to determine a slope of the envelope at each of the stored envelope values. All relative maxima in the stored envelope values are identified. A range of stored envelope values corresponding to each relative maximum is determined. The identified relative maxima are compared to locate an absolute maximum in the stored envelope values. The coagulation characteristic is then calculated from the stored envelope values within the predetermined range of envelope values corresponding to the absolute maximum.

53 Claims, 33 Drawing Sheets

U.S. PATENT DOCUMENTS

| | | | |
|---|---|---|---|
| 4,558,589 | 12/1985 | Hemmes | 73/64.42 |
| 4,599,219 | 7/1986 | Cooper et al. | 422/61 |
| 4,612,801 | 9/1986 | Girolami | 73/64.41 |
| 4,720,787 | 1/1988 | Lipscomb | 364/413.07 |
| 4,740,460 | 4/1988 | Sakata et al. | 435/18 |
| 4,741,612 | 5/1988 | Birngruber et al. | 351/221 |
| 4,752,449 | 6/1988 | Jackson et al. | 422/73 |
| 4,756,884 | 7/1988 | Hillman et al. | 422/73 |
| 4,849,340 | 7/1989 | Oberhardt | 435/13 |
| 4,876,069 | 10/1989 | Jochimsen | 422/73 |
| 4,963,498 | 10/1990 | Hillman et al. | 436/69 |
| 4,964,728 | 10/1990 | Kloth et al. | 356/427 |
| 5,047,211 | 9/1991 | Sloane, Jr. et al. | 422/73 |
| 5,053,199 | 10/1991 | Keiser et al. | 422/68.1 |
| 5,072,610 | 12/1991 | Martinoli et al. | 73/53.01 |
| 5,110,727 | 5/1992 | Oberhardt | 435/13 |
| 5,120,510 | 6/1992 | Gourley et al. | 422/82.07 |
| 5,138,872 | 8/1992 | Henderson | 73/64.41 |
| 5,140,161 | 8/1992 | Hillman et al. | 250/341 |
| 5,154,082 | 10/1992 | Mintz | 73/64.41 |
| 5,156,974 | 10/1992 | Grossman et al. | 436/69 |
| 5,167,145 | 12/1992 | Butler et al. | 73/64.43 |
| 5,181,415 | 1/1993 | Esvan et al. | 73/54.28 |
| 5,193,543 | 3/1993 | Yelderman | 128/633 |
| 5,258,719 | 11/1993 | Miura et al. | 324/673 |
| 5,302,348 | 4/1994 | Cusack et al. | 422/73 |
| 5,350,676 | 9/1994 | Oberhardt et al. | 435/13 |

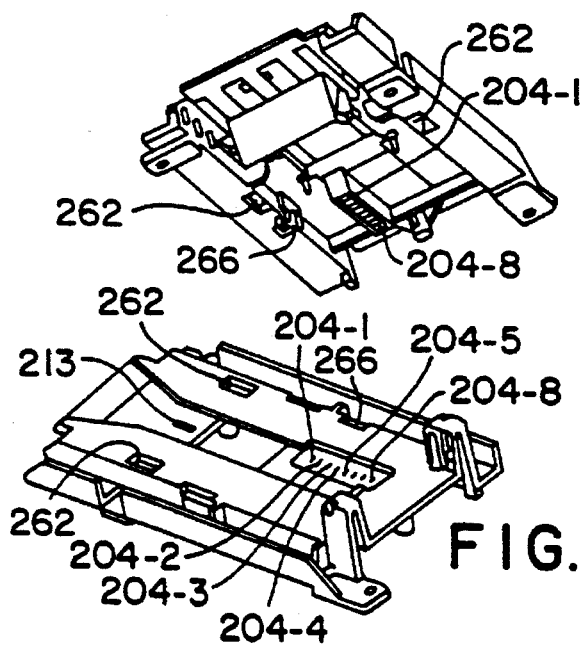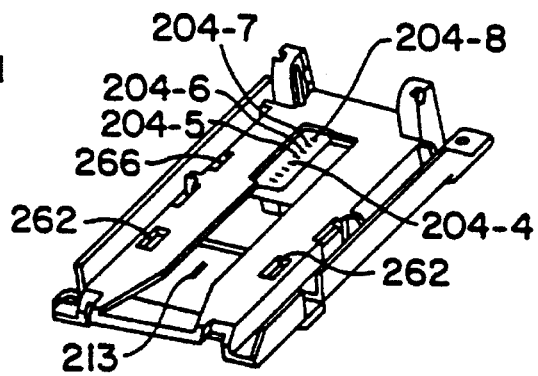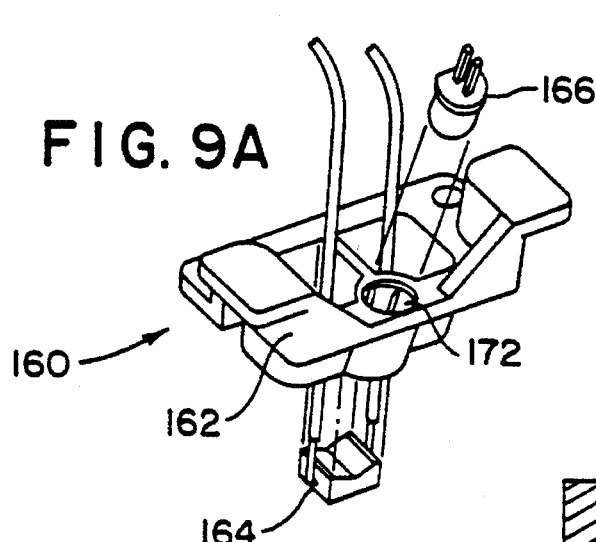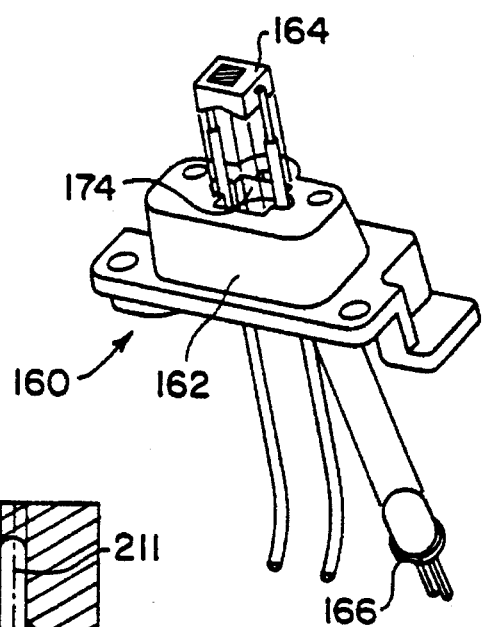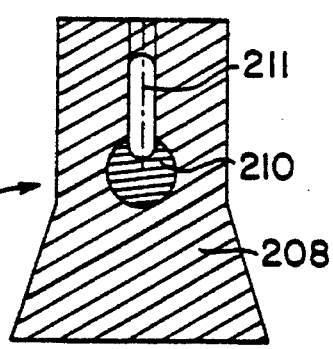

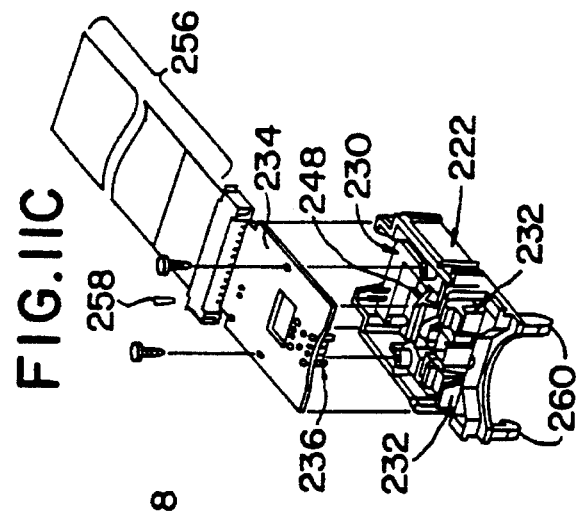
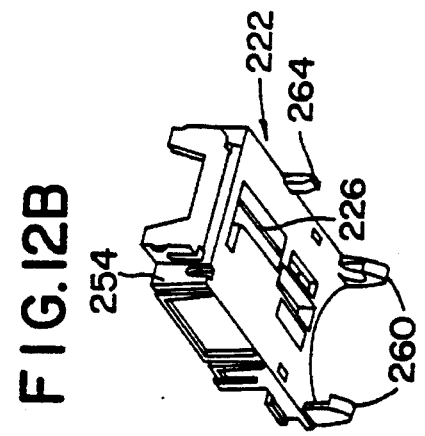
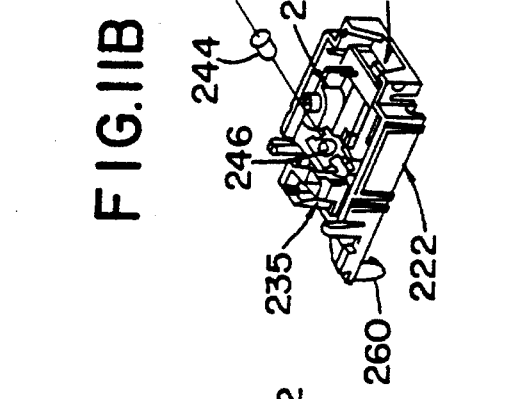
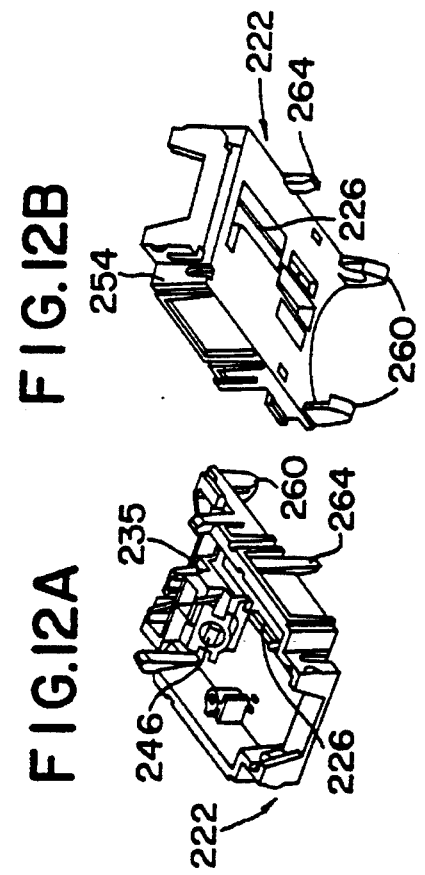
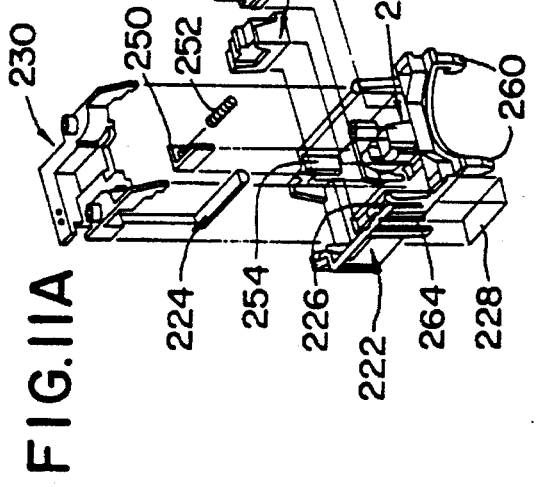
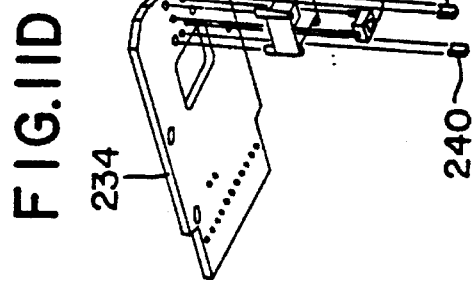

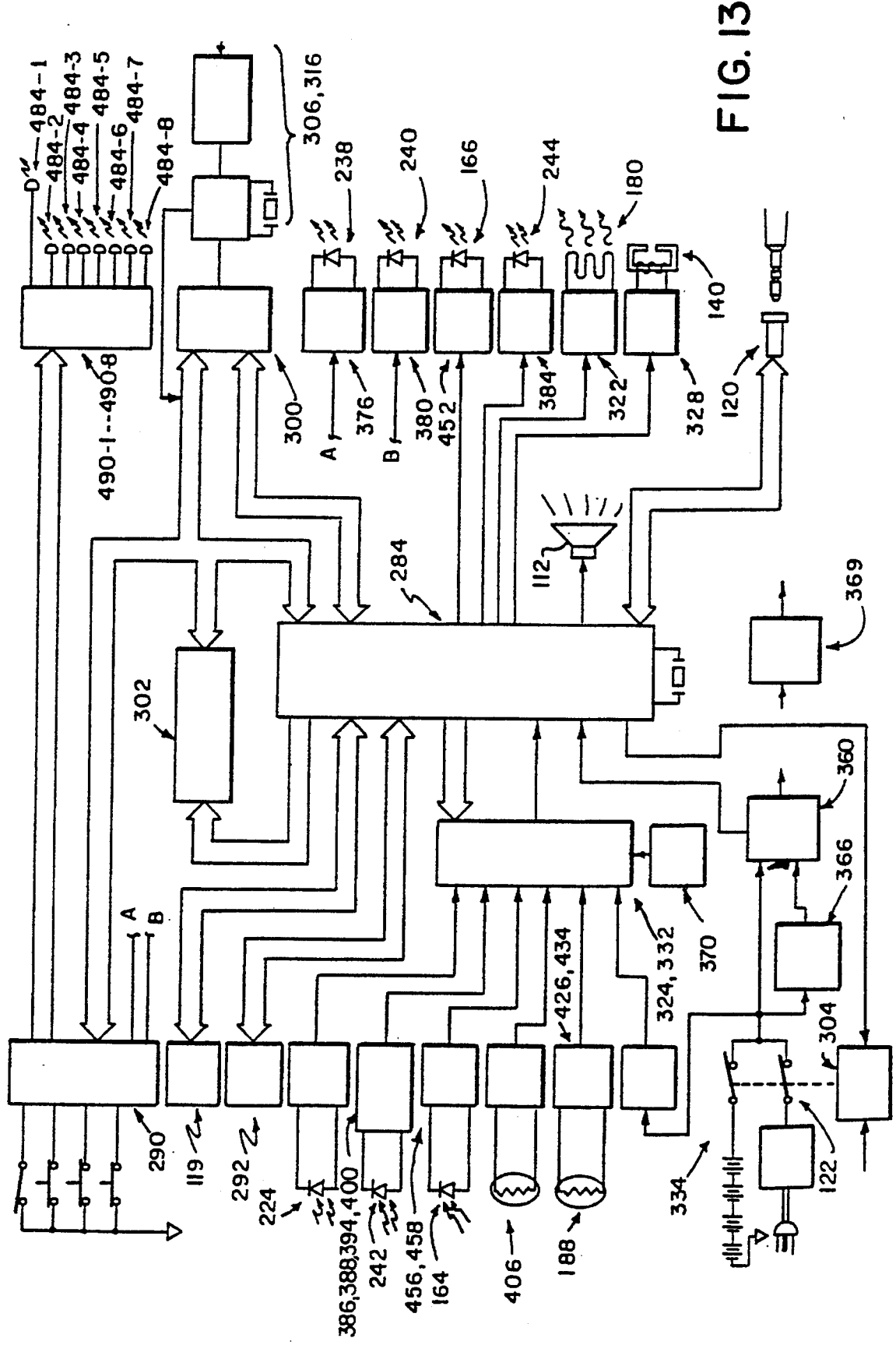

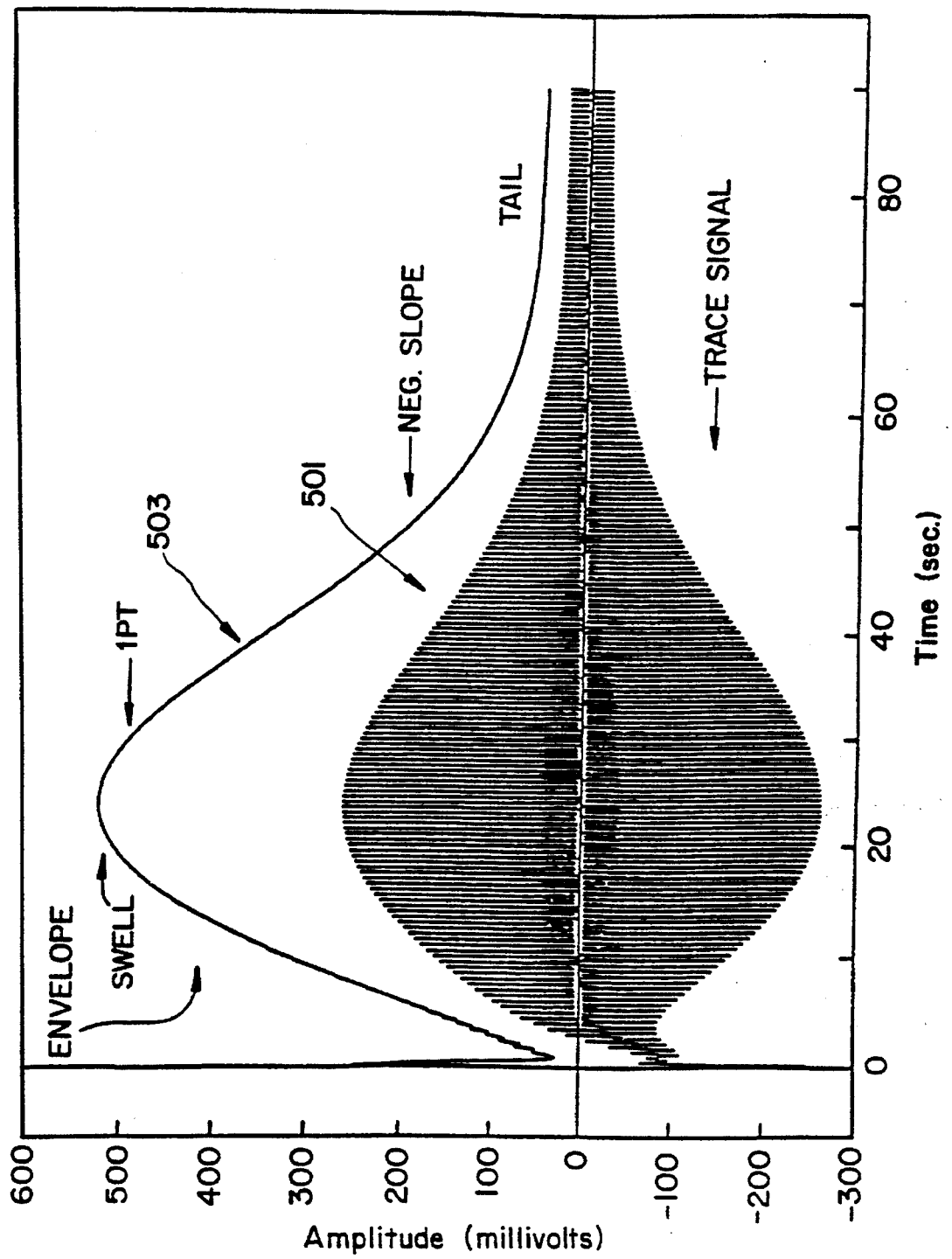

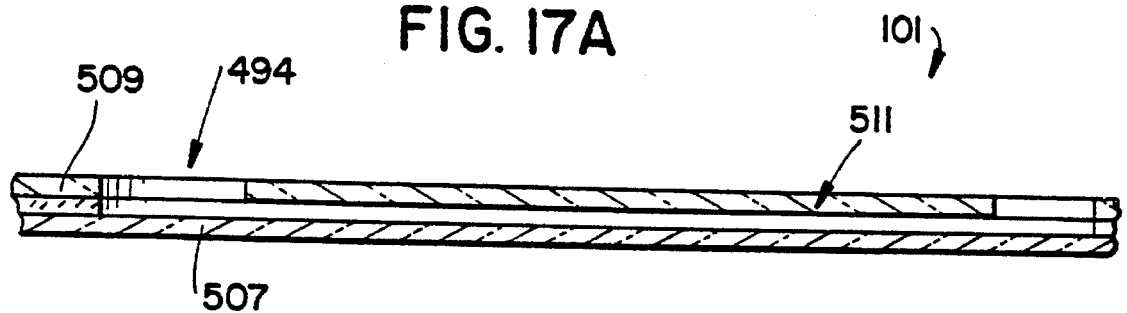
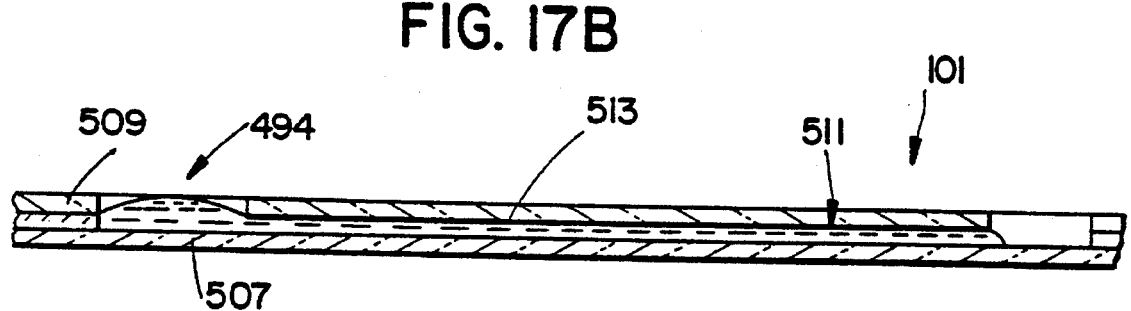

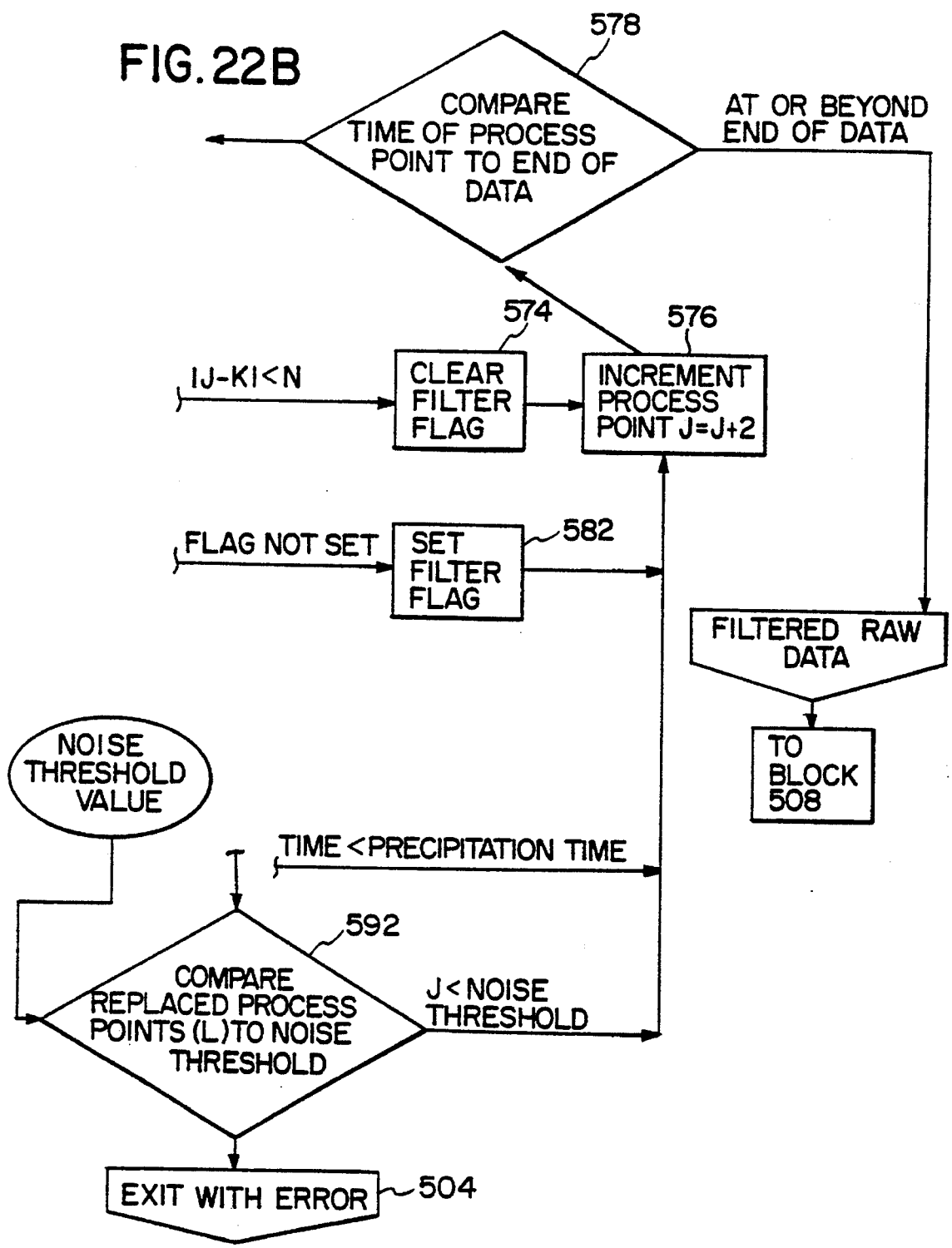

METHOD AND APPARATUS FOR CALCULATING A COAGULATION CHARACTERISTIC OF A SAMPLE OF BLOOD A BLOOD FRACTION OR A CONTROL

CROSS-REFERENCE TO RELATED APPLICATIONS

This is a related application to U.S. Ser. No. 08/114,915, titled ANALOG HEATER CONTROL FOR MEDICAL INSTRUMENT, U.S. Ser. No. 08/114,913, titled FLUID DOSE, FLOW AND COAGULATION SENSOR FOR MEDICAL INSTRUMENT, U.S. Ser. No. 08/114,914, titled POWER SUPPLY MONITOR AND CONTROL FOR MEDICAL INSTRUMENT, U.S. Ser. No. 08/114,579, titled REAGENT AND METHOD OF ITS USE, and U.S. Ser. No. 08/114,896, titled MAGNET FOR MEDICAL INSTRUMENT, all filed on the same date as this application and assigned to the same assignee, the disclosure of which is incorporated herein by reference.

BACKGROUND OF THE INVENTION

This invention relates to methods and apparatus for calculating a coagulation characteristic of samples of blood, a blood fraction, or a control.

SUMMARY OF THE INVENTION

According to one aspect of the invention, a method for calculating a coagulation characteristic of a sample of blood, a blood fraction, or a control comprises the steps of generating an output signal indicative of coagulation of the sample, sampling the output signal at a sampling rate for a predetermined time interval to provide a plurality of sampled signal values, storing the sampled values, determining an envelope from the stored signal values, storing the envelope, and calculating the coagulation characteristic from the stored envelope based on the maximum signal value.

According to another aspect of the invention, a method for calculating a coagulation characteristic of a sample of blood, a blood fraction, or a control comprises the steps of generating an output signal indicative of coagulation of the sample, sampling the output signal at a sampling rate for a predetermined time interval to provide a plurality of sampled signal values, storing the sampled signal values, identifying a maximum signal value from among the stored sampled signal values and identifying a stored sampled signal value which is a predetermined percentage less than said maximum signal value, said coagulation characteristic being related to the number of stored samples between the beginning of the sampling interval and the thus-identified stored sampled signal value.

According to yet another aspect of the invention, a method for calculating a coagulation characteristic of a sample of blood, a blood fraction, or a control comprises the steps of generating an output signal indicative of coagulation of the sample, sampling the output signal at a sampling rate for a predetermined time interval to provide a plurality of sampled signal values, storing the sampled signal values, rectifying the stored sampled signal values to provide a plurality of envelope values, storing the envelope values, examining the stored envelope values in reverse time order to determine a slope of the envelope at each of the stored envelope values, identifying all relative maxima in the stored envelope values and determining a range of stored envelope values corresponding to each relative maximum, comparing the identified relative maxima to locate an absolute maximum in the stored envelope values and calculating the coagulation characteristic from the stored envelope values within the determined range of envelope values corresponding to the absolute maximum.

According to another aspect of the invention, an apparatus for calculating a coagulation characteristic of a sample of blood, a blood fraction, or a control comprises means for generating an output signal indicative of coagulation of the sample, and means for sampling the output signal at a sampling rate for a predetermined time interval to provide a plurality of sampled signal values, for storing the sampled signal values, for determining an envelope from the stored signal values, for storing the envelope, and for calculating the coagulation characteristic from the stored envelope based on the maximum signal value.

According to another aspect of the invention, an apparatus for calculating a coagulation characteristic of a sample of blood, a blood fraction, or a control comprises means for generating an output signal indicative of coagulation of the sample, means for sampling the output signal at a sampling rate for a predetermined time interval to provide a plurality of sampled signal values, for storing the sampled signal values, for identifying a maximum signal value from among the stored sampled signal values and for identifying a stored sampled signal value which is a predetermined percentage less than said maximum signal value, said coagulation characteristic being related to the number of stored samples between the beginning of the sampling interval and the thus-identified stored sampled signal value.

According to yet another aspect of the invention, an apparatus for calculating a coagulation characteristic of a sample of blood, a blood fraction, or a control comprises means for generating an output signal indicative of coagulation of the sample, means for sampling the output signal at a sampling rate for a predetermined time interval to provide a plurality of sampled signal values, for storing the sampled signal values, for rectifying the stored sampled signal values to provide a plurality of envelope values, for storing the envelope values, for examining the stored envelope values in reverse time order to determine a slope of the envelope at each of the stored envelope values, for identifying all relative maxima in the stored envelope values, for determining a range of stored envelope values corresponding to each relative maximum, for comparing the identified relative maxima to each other to locate an absolute maximum in the stored envelope values, and for calculating the coagulation characteristic from the stored signal values within the determined range of envelope values corresponding to the absolute maximum.

BRIEF DESCRIPTION OF THE DRAWINGS

The invention may best be understood by referring to the following description and accompanying drawings which illustrate the invention. In the drawings:

FIGS. 8a–c illustrate a top perspective view, a different top perspective view, and a bottom perspective view, respectively, of a detail of FIG. 5;

FIGS. 9a–b illustrate an exploded bottom perspective view and an exploded top perspective view, respectively, of a detail of FIG. 5;

FIG. 10 illustrates a top plan view of a detail of FIG. 5;

FIGS. 11a–d illustrate exploded perspective views of details of FIG. 4;

FIGS. 12a–b illustrate perspective views from two different perspectives of a detail of FIG. 4;

FIG. 13 illustrates a block diagram of the electrical system of the instrument of FIG. 1;

FIG. 16 illustrates a reflected light signal and a rectified reflected light envelope according to the present invention;

FIGS. 17a–b illustrate enlarged fragmentary longitudinal sectional views taken generally along section lines 17—17 of FIG. 4;

DESCRIPTION OF AN ILLUSTRATIVE EMBODIMENT

Figure 1:
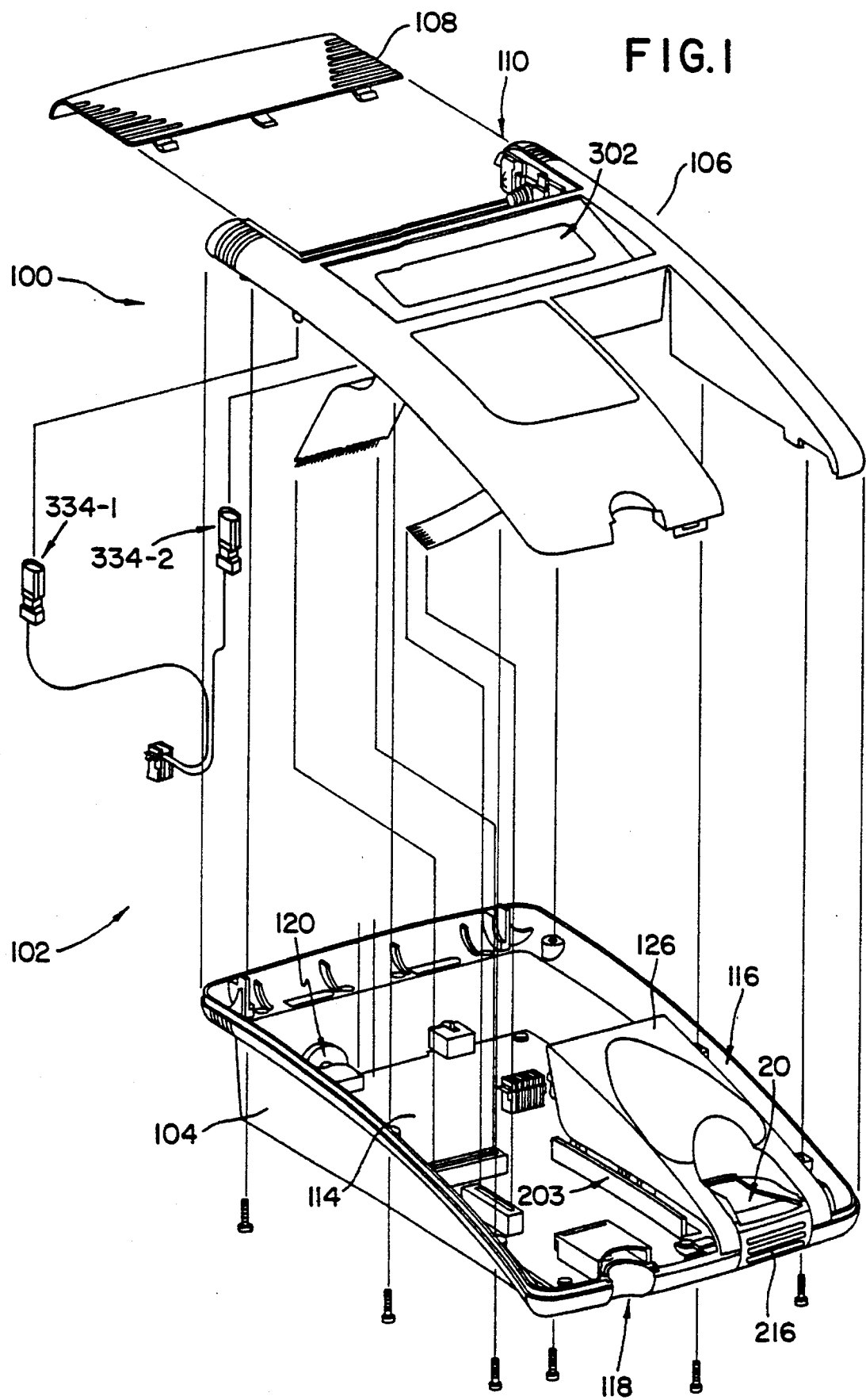
FIG. 1 illustrates an exploded perspective view of an instrument constructed according to the present invention.
Figure 2:
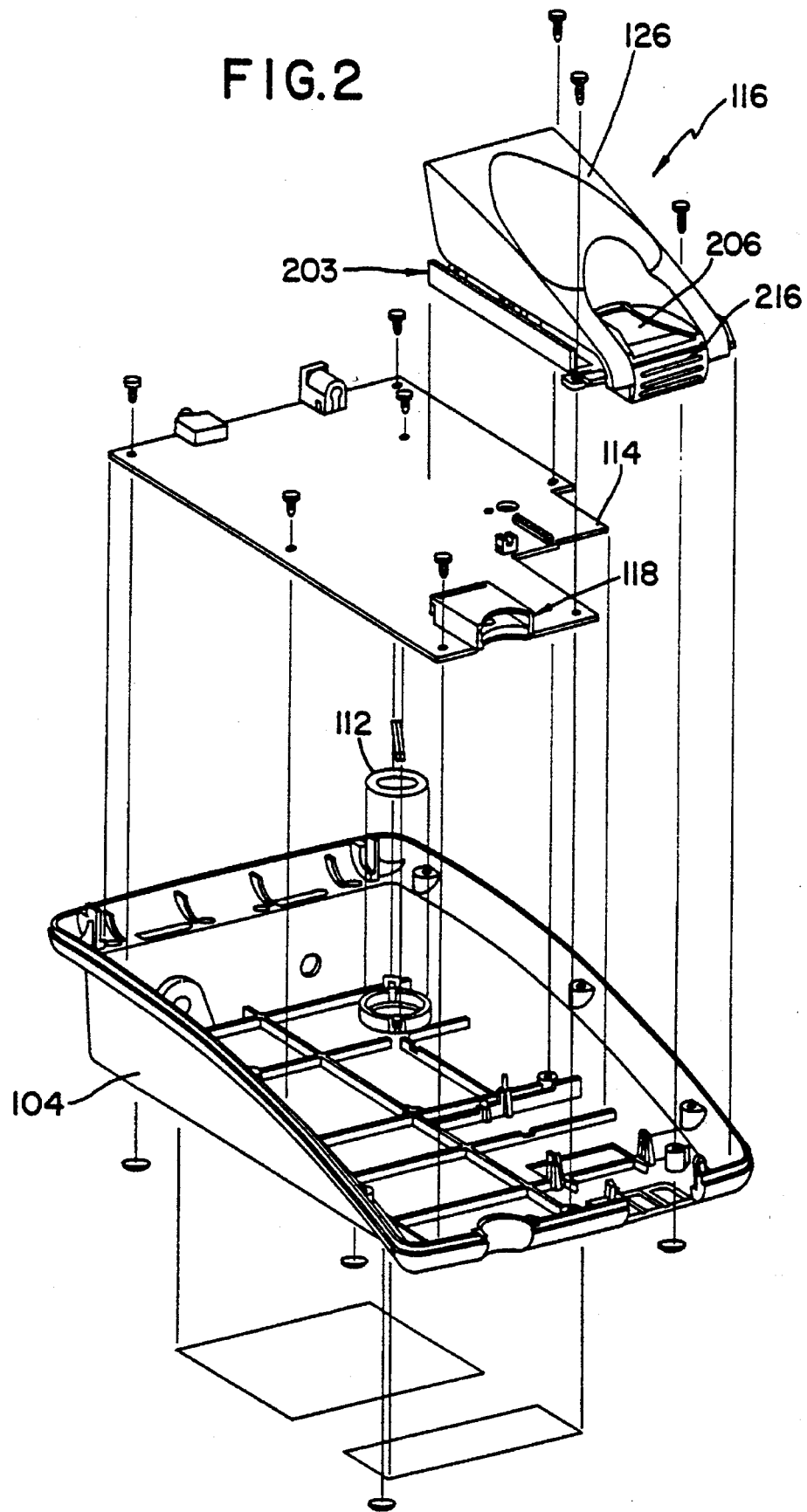
FIG. 2 illustrates a fragmentary exploded perspective view of the bottom portion of the instrument illustrated in FIG. 1.
Figure 3:
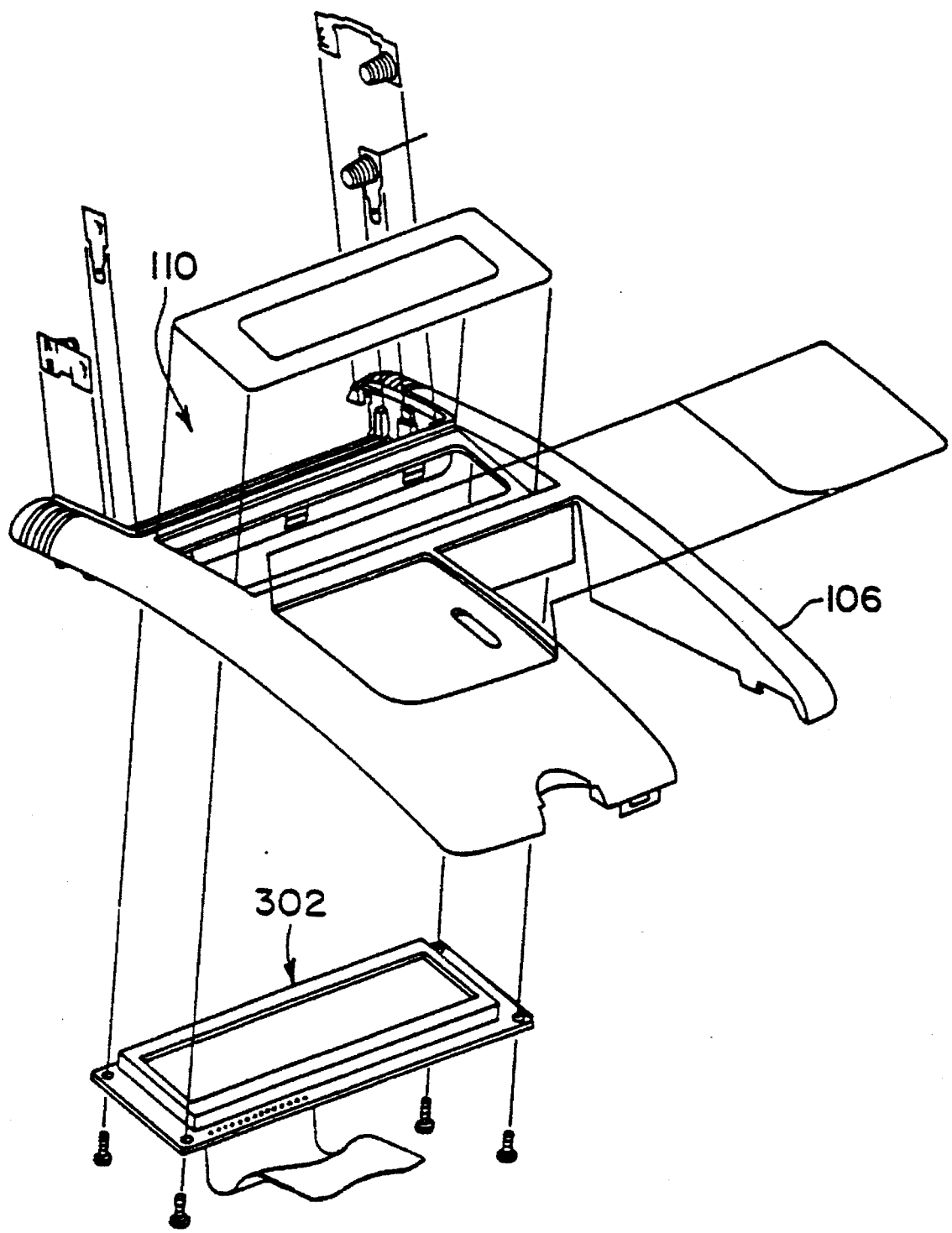
FIG. 3 illustrates a fragmentary exploded perspective view of the top portion of the instrument illustrated in FIG. 1.

The following schematic and block circuit diagram descriptions identify specific integrated circuits and other components and in many cases specific sources for these. Specific terminal and pin names and numbers are generally given in connection with these for the purposes of completeness. It is to be understood that these terminal and pin identifiers are provided for these specifically identified components. It is to be understood that this does not constitute a representation, nor should any such representation be inferred, that the specific components or sources are the only components available from the same or any other sources capable of performing the necessary functions. It is further to be understood that other suitable components available from the same or different sources may not use the same terminal/pin identifiers as those provided in this description.

An instrument 100 for determining the coagulation time of a specimen, whether of blood or of a control, includes a housing 102 comprising a housing bottom 104 and a housing top 106. Top 106 is provided with a battery door 108 which covers a battery well 110 housing the instrument 100's battery power source (not shown). Bottom 104 houses a piezoelectric beeper 112, and a printed circuit board (PCB) 114 onto which are assembled various circuit components which will be described later. An optics assembly 116, a socket 118 for a test parameters electronically erasable programmable read-only memory (EEPROM) key 119 of the type described in U.S. Pat. No. 5,053,199, a socket 120 for serial data communication, and a power supply connector 122 for connection of instrument 100 to an external AC/DC adapter (not shown) for operation thereby in lieu of the batteries (not shown) with which instrument 100 is typically equipped, are also assembled onto PCB 114.

Optics assembly 116 includes a covered 126 strip adapter top assembly 132 hinged 128 to a strip adapter bottom assembly 130. Strip adapter bottom assembly 130 includes a magnet assembly 140 held to bottom assembly 130 by a spring clip retainer 142. Magnet assembly 140 includes an 850 turn (#32 A.W.G.) coil 144 wound on a bobbin 146 which is positioned over the center leg 148 of a 50% nickel/50% iron powdered metal E-core 150. The end legs 152 of E-core 150 lie outside coil 144. A nine-and-one-half pole per end, flat plate, barium ferrite bias magnet 154 is placed over the end of the center leg 148 and is supported on one end of the bobbin 146. A connector 156 permits electrical connections to be made to coil 144.

Strip adapter bottom assembly 130 also includes a sample port housing assembly 160 having a housing 162 within which are mounted a photodiode 164 and a LED 166. Photodiode 164 senses light generated by LED 166 and reflected from the sample and strip 101 to provide an indication that a sample, be it blood or control, has been applied to instrument 100 for testing. A connector 168 provides for electrical connections to photodiode 164 and LED 166. A clamp 170 retains LED 166 in housing 162. The angle between the axes of the LED 166 and photodiode 164 openings 172, 174, respectively, is about 15°.

Strip adapter bottom assembly 130 also includes a heater assembly 180 including a heater foil 182 constructed from two polyamide films between which is sandwiched a copper nickel foil trace 183. A thermal fuse 184 and a thermistor 188 are mounted on the side of the foil 182 opposite the heater trace. Thermal fuse 184 is coupled through the foil 182 between one terminal 186 of the heater foil trace and the —HEATER terminal of a heater circuit. Contact is made to the leads of thermistor 188 from the thermistor + and − leads of the heater circuit through a hole 190 in the foil 182. An aluminum nitride heater plate 192 having a light reflecting top surface 194 is attached to foil 182 over the heater pattern area 193 of the heater trace using a thermosetting acrylic adhesive. Electrical connections are made to heater assembly 180 through a connector 196.

A transparent polycarbonate window 200 is adhesively attached to a region 202 of strip adapter bottom assembly housing 203 which is formed with a series of eight transversely extending slit openings 204-1—204-8, respectively. A transparent polycarbonate window 206 is provided with an opaque glossy black coating 208 over part of its surface and an opaque glossy yellow coating 210 over part of its surface. The remainder 211 of window 206 remains transparent. Remainder 211 overlies a slit 213 in housing 203 through which radiation from LED 166 is transmitted to the sample and through which remission from the sample is detected by photodiode 164. The yellow region 210 visible to the user of instrument 100 indicates where the sample, be it blood or control, is to be placed on a transparent disposable strip 101, such as those illustrated and described in U.S. Pat. No. 4,849,340 or the CoaguChek™ coagulation system test strip available from Boehringer Mannheim Corporation, 9115 Hague Road, Indianapolis, Ind. 46250, when the disposable strip 101 is properly located in the optics assembly 116. A push-button latch 214 including a button 216 biased into locking position by a scissors-shaped compression spring 218 completes strip adapter bottom assembly 130.

Strip adapter top assembly 132 includes a strip adapter top 222 into which is mounted a bar code reading photodiode 224 with an elongated active region exposed through a slot 226 and a transparent polycarbonate window 228 adhesively mounted on the underside of top 222 to close slot 226. A photosensor bracket 230 captures photodiode 224 in position adjacent slot 226. Test strip clamps containing foam springs 232, useful in pressing test strip 101 against heater plate 192, have tabs that fit into locating openings provided therefor in the floor of top 222. Space 235 is provided between clamps 232 to accommodate a positioning bracket 236 which is mounted on the underside of PCB 234 and extends downward therefrom into space 235. START LED 238 and FILL LED 240 are mounted respectively in front of and behind positioning bracket 236 angled at about 5° to the normal plane of incidence on PCB 234. A photodiode 242 with a daylight filter is mounted on PCB 234 inside positioning bracket 236. All three of components 238, 240, 242 are exposed downward through openings provided therefor in the bottom of strip adapter top 222 of the strip adapter top assembly 132. A MAIN assay LED 244 is mounted in an opening 246 provided therefor in strip adapter top 222 and is held in place by a holding clamp 248. The leads of LED 244 are connected to PCB 234. The axis of opening 246 makes an angle of about 45° with the axis of the opening for photodiode 242 and intersects it.

A pop-up bracket 250 is spring 252-loaded into an opening provided therefor in a rear end wall 254 of strip adapter top 222 to cause the strip adapter top assembly 132 to pop up when button 216 is pushed. An eleven-conductor flat cable 256 and connector 258 make the connections between the components mounted on PCB 234 and the remaining circuits of the PCB 114. Pawl-type catches 260 extend downward from the two forward corners of strip adapter top 222. Openings 262 are provided adjacent the front corners of strip adapter bottom assembly 130 to accommodate catches 260. Cooperating tongues 263 on button 216 are urged into engagement with catches 260 by spring 218 when strip adapter bottom assembly 130 and top assembly 132 are closed together. A flag 264 which extends downward from a side edge of strip adapter top 222 extends into a slot 266 provided for this purpose in strip adapter bottom assembly 130 where flag 264 interrupts a light path from a source to a detector to indicate that the strip adapter top and bottom assemblies 132, 130, respectively, are closed together.

The electrical circuitry on PCB 114 powers and reads the various sensors included on the coagulation optics circuit 270 on PCB 234. +5 V and -5 V are supplied to circuit 270 through terminals 258-5 and 258-1, respectively, of connector 258. Unregulated voltage is supplied to terminal 258-8 of connector 258. Ground for circuit 270 is provided at terminals 258-2, 4 and 7 of connector 258. A capacitor is coupled across terminals 258-8 and 258-2, 4, 7. The anodes of LEDs 238, 240, 244 are all coupled to terminal 258-8. The cathode of LED 238 is coupled to the START terminal, terminal 258-11, of connector 258. The cathode of LED 240 is coupled to the FILL terminal, terminal 258-10, of connector 258. The cathode of LED 244 is coupled to the MAIN terminal, terminal 258-9, of connector 258.

The anodes of photodiodes 224, 242 are coupled through a resistor 273 to terminal 258-1. The cathode of photodiode 242 is coupled to the − input terminal of an operational amplifier 274. The + input terminal of operational amplifier 274 is coupled to the anodes of photodiodes 224, 242. The output terminal of operational amplifier 274 is coupled to its − input terminal through a parallel RC feedback circuit. The output terminal of operational amplifier 274 is also coupled to the DETect terminal, terminal 258-3, of connector 258.

The cathode of photodiode 224 is coupled to the − input terminal of an operational amplifier 278. The + input terminal of operational amplifier 278 is coupled to the anodes of photodiodes 224, 242. The output terminal of operational amplifier 278 is coupled to its − input terminal through a parallel RC feedback circuit. The output terminal of differential amplifier 278 is also coupled to the CodeBaR OUTput terminal, terminal 258-6, of connector 258.

A +V terminal of a 2.5 V reference voltage source 279 is coupled to terminals 258-2, -4 and -7 of connector 258. The − terminal of reference voltage source 279 is coupled to the anodes of photodiodes 224, 242, to the + input terminals of operational amplifiers 274, 278, and through resistor 273 to the −5 V terminal, 258-1, of connector 258.

The electric circuitry 280 mounted on PCB 114 processes the various signals from circuitry 270, as well as others which circuitry 280 generates itself or receives from the user of instrument 100, or which are generated externally to instrument 100. An eight-bit microcontroller (μC) 284 has data terminals P0.0–P0.7 coupled to DATA lines 0–7, respectively, of an instrument 100 bus 286. μC 284 address terminals P2.0–P2.4 and P2.6–P2.7 are coupled to address lines A8–A12 and A14–A15, respectively, of bus 286. The $\overline{\text{ReaD}}$ and $\overline{\text{WRite}}$ terminals, P3.7 and P3.6, respectively, of vC 284, are coupled to the $\overline{\text{Read Data}}$ and $\overline{\text{Write Data}}$ lines, respectively, of bus 286. An Address Latch Enable terminal of μC 284 is coupled to the ALE terminal of a Toshiba type TC11L003AU-1031 application specific programmable gate array integrated circuit (ASIC) 290. The TIP (transmit) terminal 120-2 of serial data port socket 120 is coupled through the parallel combination of a capacitor and a resistor to ground, and through a series resistor to the Transmit Data (TXD) terminal P3.1 of μC 284. The RING (receive) terminal 120-3 of serial data port socket 120 is coupled through the parallel combination of a capacitor and a resistor to ground and through a series resistor to the Receive Data (RXD) terminal P3.0 of μC 284. The GrouND terminal 120-1 of socket 120 is coupled to ground.

The CS terminal 118-1 of ROM key socket 118 is coupled through a 6.2 V Zener diode to ground and directly to a Code ROM IC chip Select OutPut terminal 22 of ASIC 290. The SK terminal, 118-2, of ROM key socket 118 is coupled through a Zener diode to ground and directly to the CLOCK terminal, terminal P1.0, of μC 284. It is also coupled to the SK terminal of an EEPROM 292 internal to instrument 100. EEPROM 292 generally contains the meter 100 characterizing parameters. The DI and DO terminals, terminals 118-3 and 4, of socket 118 are coupled to each other, to ground through a Zener diode, directly to the DI and DO terminals of EEPROM 292, and directly to the EEDI/DO terminal P3.5, of μC 284. Terminal 118-5 of socket 118 is coupled to ground. Terminal 118-8 of socket 118 is coupled to the system +5 V supply.

The time base for μC 284 is generated by a crystal which is coupled across terminals X1–X2 thereof. A capacitor is coupled between each terminal of the crystal and ground. Terminal P1.5 of μC 284 is coupled to a resistive voltage divider including two series resistors in a beeper 112 driver circuit 294. The common terminal of these series resistors is coupled to the base of a driver transistor 296. The collector of transistor 296 is coupled through a pull-up resistor to +5 V and directly to one terminal of beeper 112. The emitter of transistor 296 and the other terminal of beeper 112 are both coupled to ground. Two diodes clamp the collector of transistor 296 between ground and +5 V.

The data terminals D0–D7 of an 8 K by 8 static random access memory (SRAM) 300 are coupled to the DATA 0-DATA 7 lines, respectively, of bus 286. The address terminals A0-A12 of SRAM 300 are coupled via the system bus 286 to the A0–A7 terminals of ASIC 290 and the A8–A12 terminals of μC 284, respectively. The $\overline{\text{ReaD}}$ and $\overline{\text{WRite}}$ terminals of SRAM 300 are coupled via the bus 286 to the $\overline{\text{ReaD}}$ and $\overline{\text{WRite}}$ terminals, respectively, of μC 284. The CE2 terminal of SRAM 300 is coupled to the junction of a resistor and a capacitor. The other terminal of the resistor is coupled to +5 V. The other terminal of the capacitor is coupled to ground. The CE2 terminal is clamped via a diode to +5 V. The DATA 0-DATA 7 terminals of a two line by sixteen character display 302 are coupled to the DATA 0-DATA 7 terminals of bus 286. The DISPlay ENable terminal of display 302 is coupled via bus 286 to the DISPlay ENable terminal of ASIC 290. The A0–A1 terminals of display 302 are coupled to the A0–A1 terminals, respectively, of bus 286. The GrouND terminal of display 302 is coupled to the system ground and the VDD terminal of display 302 is coupled to +5 V. Terminal 3 of display 302 is coupled through a resistor to ground and through a resistor to +5 V. An instrument 100 keypad switch has its ON/OFF terminal connected to the source of a field effect transistor (FET) 303 in instrument 100's power supply circuit 304. The YES terminal of the switch is coupled to InPut terminal 1 of ASIC 290. The NO terminal of the switch is coupled to InPut terminal 2 of ASIC 290. The YES and NO terminals are also coupled through respective pull-up resistors to +5 V.

Battery back-up protection is provided to SRAM 300 by a circuit including a 3.3 V regulator 306. The $V_{in}$ terminal of regulator 306 is coupled to the junction of a resistor and a capacitor. The other terminal of the capacitor is coupled to ground. The other terminal of the resistor is coupled to the cathode of a diode, the anode of which is coupled to +VBAT. The $V_{out}$ terminal of regulator 306 is coupled across a series resistive voltage divider including a resistor 308 and a resistor 310 to ground. $V_{out}$ is also coupled to the emitter of a transistor 312. The junction of resistors 308, 310 is coupled to the base of a transistor 314. The emitter of transistor 314 is coupled to ground. Its collector is coupled through a series resistor to the base of transistor 312. The collector of transistor 312 is coupled to the BATtery 1 terminal of a real time clock 316, and to one terminal of a capacitor, the other terminal of which is coupled to ground. The D and Q terminals of IC 316 are coupled to the DATA 0 line of bus 286. The $\overline{\text{CEI}}$, $\overline{\text{CEO}}$, $\overline{\text{WE}}$ and $\overline{\text{OE}}$ terminals of IC 316 are coupled to terminal P2.7(A15) of μC 284, terminal $\overline{\text{CE}}$ of SRAM 300, the $\overline{\text{Write Data}}$ line of bus 286, and the $\overline{\text{Read Data}}$ line of bus 286, respectively. The VCC OUTPUT terminal of IC 316 is coupled to the VDD terminal of SRAM 300 and through a capacitor to ground. The time base for IC 316 is generated by a crystal coupled across terminals X1–X2 thereof.

The PoWeR INTerrupt, MAIN ConTroL, HeaTeR ON/OFF, A/D OUT, A/D A, A/D B, power SUPPLY ON, SAMPLE ConTroL, and MAGnet 1 ConTroL terminals, terminals P3.2, P3.3, P3.4, P1.1, P1.2, P1.3, P1.4, P1.6 and P1.7, respectively of μC 284, are coupled to the power supply circuit 304, the main LED driver in an LED driver circuit 320, the heater control circuit 322, the COMParator OUTput terminal of a Teledyne type TSC500ACOE A/D converter IC 324 in the analog section of instrument 100, the A terminal of A/D 324, the B terminal of A/D 324, power supply circuit 304, the sample port circuit 326, and the magnet current control circuit 328.

The InPut 3 terminal of ASIC 290 is coupled to an optical switch 486. The OutPut 10–17 terminals of ASIC 290 are coupled to the bar code LED array driver circuit 330. The OutPut terminals 20, 21, 24 and 25 of ASIC 290 are coupled to the setpoint temperature control of heater driver circuit 322, the LATCH ENABLE terminal of an eight-to-one analog multiplexer 332 in the analog section of instrument 100, the fill LED driver in circuit 320, and the start LED driver in circuit 320, respectively. The Address 0–2 lines of bus 286 are coupled to the A, B and C terminals, respectively, of multiplexer 332.

Power supply circuit 304 includes an instrument 100 battery connector 334 having +VBAT terminal 334-1 and ground terminal connector 334-2 and AC/DC converter power supply connector 122 having +VIN terminals 122-3 and 6 connected together and GRouNd terminals 122-1 and 4 connected together. +VBAT is coupled through a series resistor to the gate of FET 303. The drain of FET 303 is coupled through two series resistors 336, 338 to the base of a transistor 340. The emitter of transistor 340 is coupled to its base through the series combination of a resistor and a diode, through a diode and fuse to +VIN, and through a parallel combination of a transient suppressor diode, a resistor and a capacitor to ground. The junction of resistors 336, 338 is coupled through a resistor to the base of a transistor 342. The emitter of transistor 342 is coupled to the base of transistor 340. The collector of transistor 342 is coupled through two series resistors to ground. The common terminal of these resistors is coupled to the base of a transistor 346. The emitter of transistor 346 is coupled to ground and its collector is coupled through a pull-up resistor to +5 V. The collector of transistor 346 is also coupled to InPut terminal 0 of ASIC 290.

The emitter of a transistor 350 is coupled to +VBAT. +VBAT is coupled through a resistor and a diode in series to the base of transistor 350. The base of transistor 350 is coupled through a diode 351 to the base of transistor 340. The base of transistor 340 is coupled through a parallel resistance network to the collector of a transistor 352. The emitter of transistor 352 is coupled to ground. Its base is coupled through a resistor to ground and through a resistor to the collector of a transistor 354. The emitter of transistor 354 is coupled to +5 V Analog. The base of transistor 354 is coupled through a resistor to +5 VA. The base of transistor 354 is also coupled through a resistor to terminal P1.4 of μC 284. Once the on/off key to meter 100 is depressed upon turn-on, enough time is given for the +5 V supply to come up and the μC 284 to reset itself (once +5 V supply has been applied to its $V_{cc}$ pin) and then to have terminal P1.4 of μC 284 latch the system +5 V supply on. This terminal is also used to shut the system down in an orderly fashion. VUN-REGulated appears at the collector of transistor 350 and at the cathode of a diode 356, the anode of which is coupled to the collector of transistor 340.

Regulation is initiated by battery voltage +VBAT on the gate of FET 303. If the battery is in backward, or is below minimum regulation level and no AC/DC adapter is connected to instrument 100, or is missing and no AC/DC adapter is connected to instrument 100, the instrument 100 cannot be turned on. If the battery is installed properly and is above minimum regulation level, regulation is established at the base of transistor 340 and, through diode 351, at the base of transistor 350. Regulation is also signalled through transistors 342 and 346 to the ON/OFF INDicator InPut terminal 0 of ASIC 290. If the battery voltage +VBAT is greater than +VIN, diode 356 decouples the AC/DC adapter input circuity, including transistor 340 and its associated regulating circuitry from VUNREGulated so that the battery does not power that circuitry.

VUNREGulated is supplied to the VIN terminal of a +5 V regulator IC 360. VUNREGulated is also supplied to a series voltage divider including a resistor 362 and a resistor 364. The common terminal of resistors 362, 364 is coupled to the INput terminal of a voltage detector IC 366. The ERROR output terminal of IC 366 is coupled through a resistor to VUNREGulated and through a resistor to the base of a transistor 368. The collector of transistor 368 is coupled through a load resistor to VUNREGulated and is coupled directly to the SHUTDOWN terminal of +5 V regulator IC 360. If the supply voltage is low, IC 366 will prevent instrument 100 from being turned on. Regulated +5 V for the digital circuitry of instrument 100 appears at the VOUT terminal of +5 V regulator IC 360. The SENSE terminal of IC 360 is coupled to +5 V. The ERROR terminal of IC 360 is coupled through a pull up resistor to +5 V. The ERROR terminal is also coupled to the PoWeRINTerrupt terminal, P3.2, of µC 284. The error terminal's main function is to warn the µC 284 that the system power is approaching an unregulated condition. By warning µC 284 of such condition, µC 284 can power down the system in an orderly fashion prior to any soft failures occurring. A capacitor across VOUT and GrouND of IC 360 is decoupled by a resistor from a tantalum capacitor across the +5 VAnalog supply to analog ground. The voltage across the VOUT output terminal to ground is fed back through a diode and resistor in series to the base of transistor 368. The VOUT output terminal of IC 360 is also coupled to the V+ terminal of a +5 V-to—5 V converter 369. A tantalum capacitor is coupled across the CAP+ and CAP–terminals of converter 369. –5 VDC for circuits requiring it appears across the VOUT terminal of converter 369 to ground. The instrument 100's analog and digital grounds are tied together here. A +V terminal of a 2.5 V reference voltage source 370 is coupled through a resistor to +5 VAnalog. 2.5 VREFerence is established across the +V terminal of source 370 and ground.

Turning now to the LED driver circuitry 320 for the optical head assembly 116, the start LED control OutPut terminal 25 of ASIC 290 is coupled through a diode to the − input terminal of an operational amplifier 374. The + input terminal of operational amplifier 374 is coupled to VREF. The output terminal of operational amplifier 374 is coupled to the base of a transistor 376. The collector of transistor 376 is coupled to the START LED terminal, terminal 258-11, of connector 258. The emitter of transistor 376 is coupled to ground through a resistor, which limits the current through the start LED at a constant current, and through a feedback resistor to the − input terminal of operational amplifier 374.

The FILLConTroL terminal, OutPut terminal 24, of ASIC 290 is coupled through a diode to the − input terminal of an operational amplifier 378. The + input terminal of operational amplifier 378 is coupled to VREF. The output terminal of operational amplifier 378 is coupled to the base of a transistor 380, the collector of which is coupled to the FILL LED terminal, terminal 258-10, of connector 258. The emitter of transistor 380 is coupled through a parallel resistor network to ground, which limits the current through the fill LED at a constant current, and through a feedback resistor to the − input terminal of operational amplifier 378.

The MAIN ConTroL terminal, P3.3, of µC 284 is coupled through a diode to the − input terminal of an operational amplifier 382. The + input terminal of operational amplifier 382 is coupled to VREF. The output terminal of operational amplifier 382 is coupled to the base of a Darlington-coupled transistor pair 384. The collectors of transistors 384 are coupled to the MAIN assay LED terminal, 258-9, of connector 258. The emitter of transistors 384 is coupled through a resistor to ground, which limits the current through the main LED at a constant current, and through a resistor, to the − input terminal of operational amplifier 382.

The sensed bar code of the disposable test strip 101 which is being used in a particular test comes in to circuit 320 serially on the CodeBaR terminal, 258-6, of connector 258. It is coupled directly to analog input terminal X5 of multiplexer 332. The START, FILL and MAIN assay DETect signals indicating that an adequate volume sample droplet has been placed over yellow area 210 on a test strip 101, and its raw coagulation results data, are provided from terminal 258-3 of connector 258 to the + input terminals of two operational amplifiers 386, 388. Operational amplifier 386 is configured as a unity gain buffer and its output terminal is coupled to the DC input terminal X1 of multiplexer 332. Operational amplifier 388 is also configured as a unity gain buffer and its output terminal is capacitively coupled through a capacitor and two series resistors 390, 392 to a + input terminal of an operational amplifier 394. The output terminal of operational amplifier 388 is also coupled to ground through an RC parallel combination. The + terminal of operational amplifier 394 is coupled to ground through a capacitor. The output terminal of operational amplifier 394 is coupled through a feedback resistor to its − input terminal. Its − input terminal is coupled to ground through a resistor. The output terminal of operational amplifier 394 is also coupled through series resistors 396, 398 to ground. The common terminal of resistors 396, 398 is coupled through a capacitor to the common terminal of resistors 390, 392.

The signal at the output terminal of operational amplifier 394 is directly coupled to the X0 input terminal, AC1, of multiplexer 332. That signal is also coupled to the + input terminal of an operational amplifier 400. The signal at the output terminal of operational amplifier 400 is directly coupled to the X2 input terminal, AC2, of multiplexer 332. The output terminal of operational amplifier 400 is also coupled through a resistor to the − input terminal thereof. The − input terminal of operational amplifier 400 is coupled through a resistor to ground.

VUNREGulated is coupled through a series voltage divider including a resistor 402 and a resistor 404 to ground. The common terminal of resistors 402,404 is coupled directly.to the analog BATTery voltage input terminal X4 of multiplexer 332. +5 VA is coupled to the VDD input terminal of a temperature sensor 406. The VOUT terminal of sensor 406 is coupled directly to the analog VTEMP voltage input terminal, X6, of multiplexer 332 and through a pull-up resistor to +5 VA.

The heater control circuit 322 includes two series resistors 410, 412 coupled between the HeaTeR ON/OFF terminal of µC 284 and ground. The common terminal of resistors 410, 412 is coupled to the base of a transistor 414, the collector of which is coupled through two series resistors 416, 418 to +5 VA, and the emitter of which is coupled to ground. The common terminal of resistors 416, 418 is coupled to the base of a transistor 420, the emitter of which is coupled to +5 VA, and the collector of which is coupled through a series resistor 422 and capacitor 424 to ground. The common terminal of resistor 422 and capacitor 424 is coupled to the − input terminal of an operational amplifier 426.

+5 VA is coupled through a series resistor, a potentiometer 428 and a resistor to ground. The movable contact of potentiometer 428 is coupled to the − input terminal of operational amplifier 426. The potentiometer enables the heater plate 192 to achieve about 39° C. +5 VA is coupled through a series resistor 430 and capacitor 432 to ground. The common terminal of resistor 430 and capacitor 432 is coupled to the THermistor + terminal, 196-3, of connector 196, and to the + input terminal of operational amplifier 426. The + input terminal of operational amplifier 426 is coupled through the series combination of a diode and a resistor to ground. The junction of the resistor and diode is coupled to the base of a transistor 434, the emitter of which is coupled to ground. The output terminal of operational amplifier 426 is coupled through a resistor to its − input terminal and through the series combination of a diode and a resistor to the collector of transistor 434.

The SETPoinT 2 terminal, OutPut terminal 20, of ASIC 290, is coupled through series resistors 436, 438 to +5 VA. The ASIC 290 provides control of the heater plate 192 temperature at two different setpoints, 39° C. and 44° C. The second setpoint is set high to permit the heater plate 192 to attain 44° C. temperature, thereby permitting more rapid warming of samples to 39° C. The common terminal of resistors 436, 438 is coupled to the base of a transistor 440, the emitter of which is coupled to +5 VA and the collector of which is coupled through a resistor to the − input terminal of operational amplifier 426. A series resistive voltage divider including a resistor 442 and a resistor 444 is coupled between the output terminal of operational amplifier 426 and ground. The common terminal of resistors 442, 444 is coupled to an analog input terminal X3 of multiplexer 332. Heater control circuit 322 operating status is thus multiplexed into μC 284. Additionally, heater control status, as reflected by the voltage at the collector of transistor 434, controls the flow of current through the heater foil 182. This is accomplished through a transistor 446, the base of which is coupled to the collector of transistor 434 and the collector of which is coupled to the − HEATER terminal, 196-2, of connector 196. The + HEATER terminal, 196-1, of connector 196 is coupled to + VUNREGulated. The emitter of transistor 446 is coupled through a parallel resistance network to ground. The base of transistor 446 is also coupled through two series diodes to ground, which limits the current through the heater foil to approximately 0.4 A. The − THermistor terminal, 196-4, of connector 196 is coupled to ground.

Terminal P1.6 of μC 284 is coupled through a diode to the − input terminal of an operational amplifier 450 in the sample port circuit 326. The + input terminal of operational amplifier 450 is coupled to VREF. The output terminal of operational amplifier 450 is coupled to the base of a transistor 452, the emitter of which is coupled through a feedback resistor to the − input terminal of operational amplifier 450 and to ground through resistance, which limits the current through the sample port LED at a constant current. The collector of transistor 452 is coupled to terminal 168-1 of the sample port connector 168. +5 VA is coupled to terminal 168-2, the VDD terminal, of connector 168. VUNREGulated is coupled to terminal 168-5 of connector 168. The SAMPle IN terminal, 168-4, of connector 168 is coupled to ground through a resistor and through a capacitor to the − input terminal of an operational amplifier 456. The + input terminal of operational amplifier 456 is coupled to ground. The output terminal of operational amplifier 456 is coupled through a parallel RC feedback circuit to its − input terminal. The output terminal of operational amplifier 456 is coupled through a capacitor to the + input terminal of an operational amplifier 458. The + input terminal of operational amplifier 458 is coupled to ground through a resistor.

The − input terminal of operational amplifier 458 is coupled to ground through a resistor. The output terminal of operational amplifier 458 is coupled to the cathode of a diode, the anode of which is coupled through a resistor to the − input terminal of operational amplifier 458. The output terminal of operational amplifier 458 is also coupled to the anode of a diode 460, the cathode of which is coupled through a resistor 462 to the − input terminal of operational amplifier 458. This provides a hysteresis-type configuration which has different gains depending upon whether the voltage at the + input terminal of operational amplifier 458 is greater than or less than the voltage at the − input terminal thereof. The common terminal of diode 460 and resistor 462 is coupled through the series combination of a resistor 464 and a capacitor 466 to ground. The common terminal of resistor 464 and capacitor 466 is coupled to the SAMPle DETect input terminal, X7, of multiplexer 332.

Terminal P1.7 of μC 284 is coupled through two series resistors in the magnet control circuit 328 to ground. The common terminal of these resistors is coupled to the base of a NPN transistor 470, the emitter of which is coupled to ground. The collector of transistor 470 is coupled through series resistors to +5 VA. The common terminal of these resistors is coupled to the base of a PNP transistor 471, the emitter of which is coupled to +5 VA and the collector of which is coupled to the − input terminal of an operational amplifier 472. The series combination of a resistor 474 and a resistor 476 is coupled between VREF and ground. A capacitor is coupled across resistor 476. The common terminal of resistors 474 and 476 is coupled to the + input terminal of operational amplifier 472.

The output terminal of operational amplifier 472 is coupled to the base of a NPN magnet coil 144-driver transistor 478. The emitter of transistor 478 is coupled through a resistor to ground, which limits the current through the magnet coil at a constant current, and through a feedback resistor to the − input terminal of operational amplifier 472. A capacitor is coupled between the − input terminal of operational amplifier 472 and ground. The collector of transistor 478 is coupled to terminal 156-3 of connector 156. Terminal 156-1 of connector 156 is coupled to VUNREGulated. Coil 144 is coupled across connectors 156-1 and 156-3. The series combination of a resistor and a capacitor is also coupled across connectors 156-1 and 156-3. A flyback diode is also coupled across terminals 156-1 and 156-3.

The bar code LED driver circuit 330 which is associated with photodiode 224 includes eight bar code-illuminating LEDs 484-1—484-8. The anode of LED 484-1 is coupled to +5 V and its cathode is coupled to the Anode terminal of optical switch 486. Optical switch 486 provides the source and detector for flag 264 to indicate when the strip adapter top and bottom assemblies 130, 132 are closed together. The collector terminal, C, of optical switch 486 is coupled to InPut terminal 3 of ASIC 290, and through a pull-up resistor to +5 V. The cathode terminal, K, of optical switch 486 is coupled through a load resistor to the collector of a transistor 490-1, the emitter of which is coupled to ground and the base of which is coupled through a resistor to OutPut terminal 17 of ASIC 290. The anodes of the remaining LEDs 484-2—484-8 are coupled through a common load resistance to +5 V. The cathodes of LEDs 484-2—484-8 are coupled to the collectors of transistors 490-2—490-8, respectively. The emitters of transistor 490-2—490-8 are coupled to ground.

The bases of transistor 490-2—490-8 are coupled through respective resistors to OutPut terminals 16-10, respectively, of ASIC 290.

LEDs 484-1—484-8 are mounted on PCB 114 and emit light through respective slit openings 204-1—204-8, respectively. LED's 484-1—484-8 are sequentially energized through transistors 490-1—490-8, respectively. The presence or absence of a bar code in region 492 of a particular test strip 101 placed in instrument 100 is sensed by transmission of light from a respective LED 484-1—484-8 by conduction of photodiode 224. This identifies certain test strip 101 lot-specific parameters for instrument 100.

In operation, a sample 513 is deposited in the test strip 101 sample well 494 over location 210. Radiation from LED 164, which is strobed at 0.25 sec. intervals, detected by photodiode 166 establishes the dosing of strip 101. START LED 238 is strobed at 50 msec. intervals until the arrival of the sample 513 at the region of strip 101 over START LED 238 is established by the radiation from START LED 238 detected by photodiode 242. The flow time of the sample 513 between the sample application point at well 494 and the detection of the arrival of the sample 513 over the START LED 238 establishes the sample 513 as blood or a control. The control solutions, being less viscous, flow between these two locations more rapidly, and this is detected by the instrument 100. The minimum flow time that the instrument 100 will interpret as blood and/or the maximum flow time that the instrument 100 will interpret as control can be varied from strip lot to strip lot by changing (a) parameter(s) in the user-insertable EEPROM key 119. This relieves the user from the need to indicate to the instrument 100 or otherwise record when a quality control check is being conducted.

After photodiode 242 has detected the arrival of the sample 513 over the START LED 238, the START LED 238 is deenergized and the FILL LED 240 is energized. The next decrease in radiation detected by photodiode 242 indicates the arrival of the sample 513 over the FILL region of the strip 101. The elapsed time between detection by photodiode 242 of arrival of the sample 513 over START LED 238 and detection by photodiode 242 of arrival of the sample 513 over FILL LED 240 is used by the instrument 100 to determine whether the volume of the sample 513 which was applied is adequate to conduct a coagulation test. If the instrument 100 determines that the applied sample 513 volume was inadequate to conduct a test, the instrument 100 provides an error message and returns to its ready state. If the instrument 100 determines that the applied sample 513 volume was sufficient to conduct a coagulation time test reliably, FILL LED 240 is deenergized and MAIN assay LED 244 is energized. Electromagnet 140 is also energized and monitoring by photodiode 242 of MAIN assay LED 244 radiation begins. Magnet assembly 140, when driven by magnet current control circuit 328, stirs ferromagnetic particles from the test strip 101 borne by the sample 513, be it blood or control. The particles reorient themselves along the combined lines of force of magnet assembly 140 and bias magnet 154 and provide a modulated light transmission profile of the sample. This transmission profile, illustrated in FIG. 16 at 501, is detected by photodiode 242 and is multiplexed (DETect--AC1-DC) via multiplexer 332 and A/D 324 into μC 284. Coagulation of the sample causes the reduction in the modulation in this transmission profile as described in U.S. Pat. Nos. 4,849,340 and 5,110,727. Waveform 501 is rectified and the envelope 503 of the rectified waveform 501 is formed.

To reduce the likelihood of double dosing the strip 101, the ratio of START to FILL time-to-sample application to START time is formed. This ratio is compared to a parameter provided from key 119. The ratio must be less than the parameter. Otherwise the instrument 100 will conclude that the strip 101 has been double dosed and will generate an error message. Double dosing is to be avoided because it can refluidize the ferromagnetic particles, producing an erroneous coagulation time reading.

Figure 4:
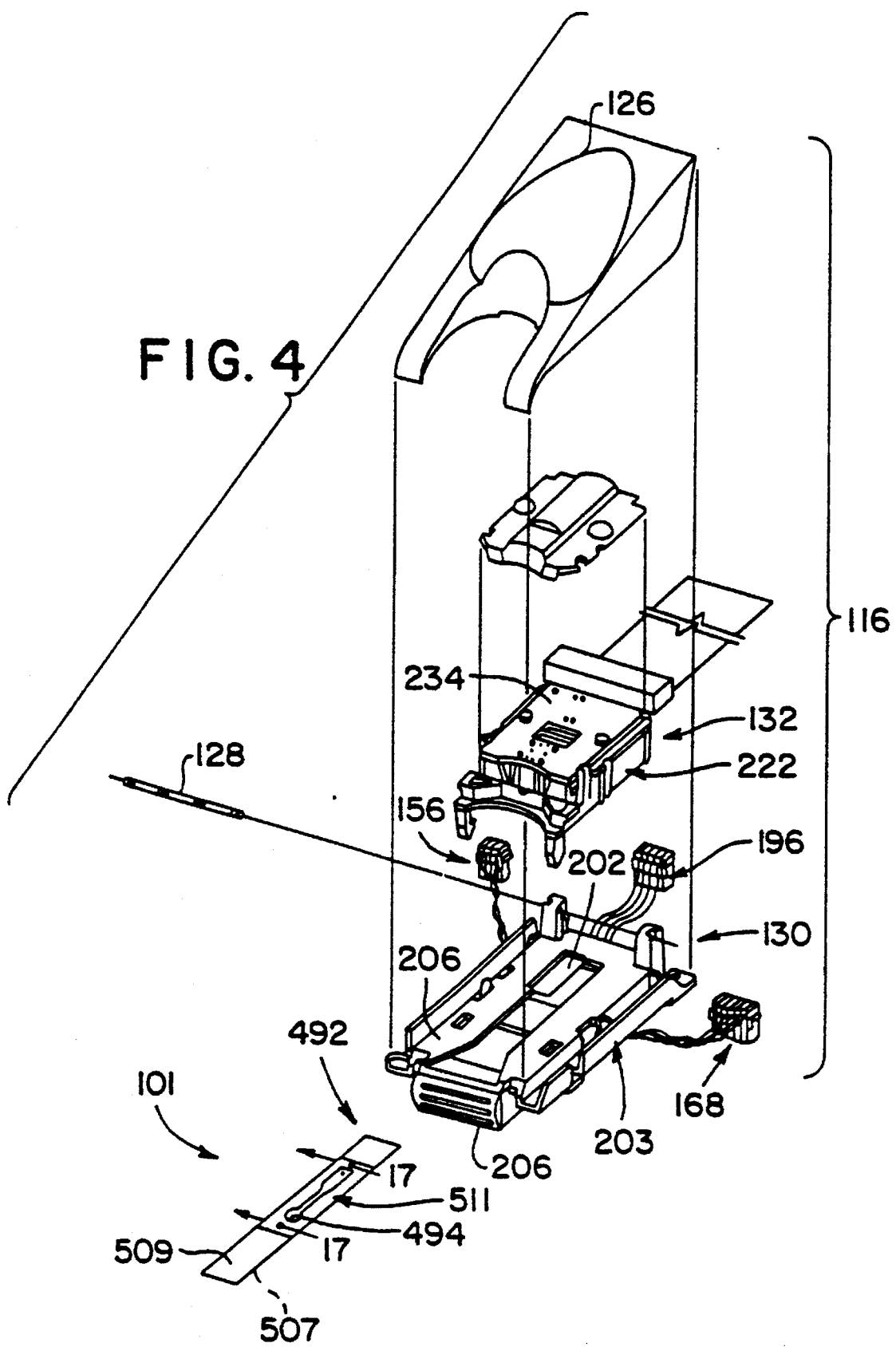
FIG. 4 illustrates an exploded perspective view of a detail of FIG. 1.
Figure 5:
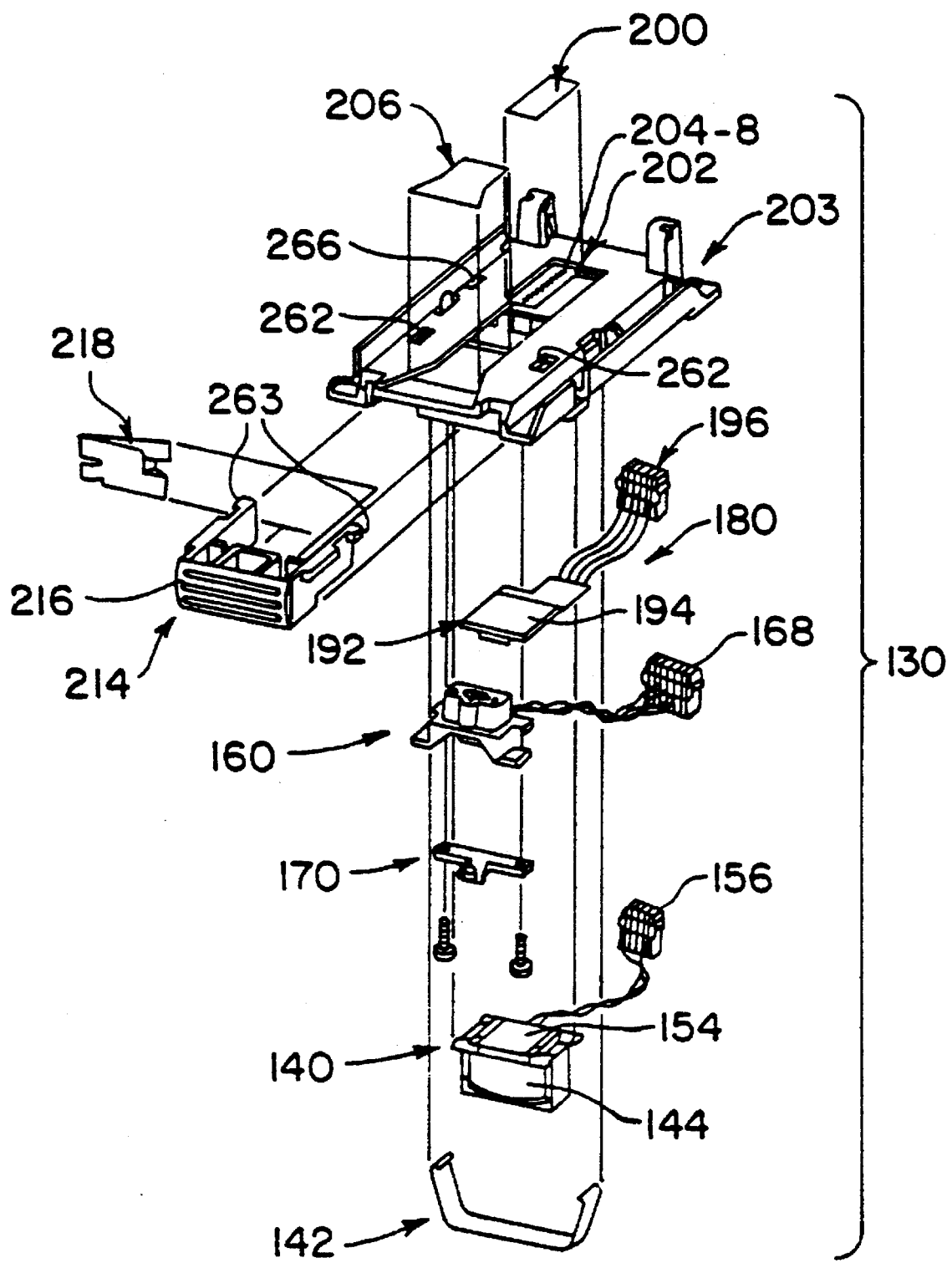
FIG. 5 illustrates an exploded perspective views of a detail of FIG. 4.
Figure 6:
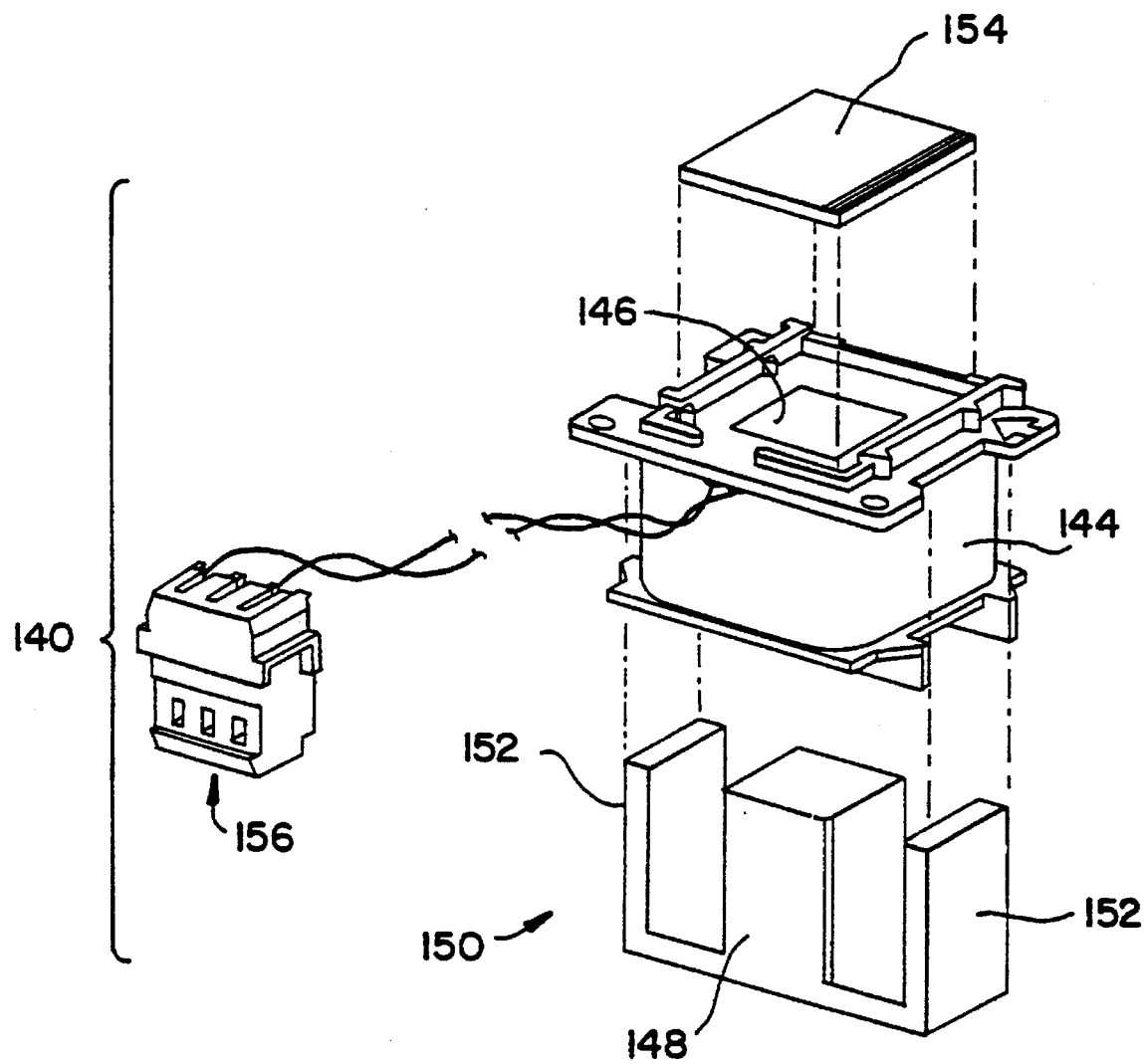
FIG. 6 illustrates an enlarged exploded perspective view of a detail of FIG. 5.
Figure 7A:
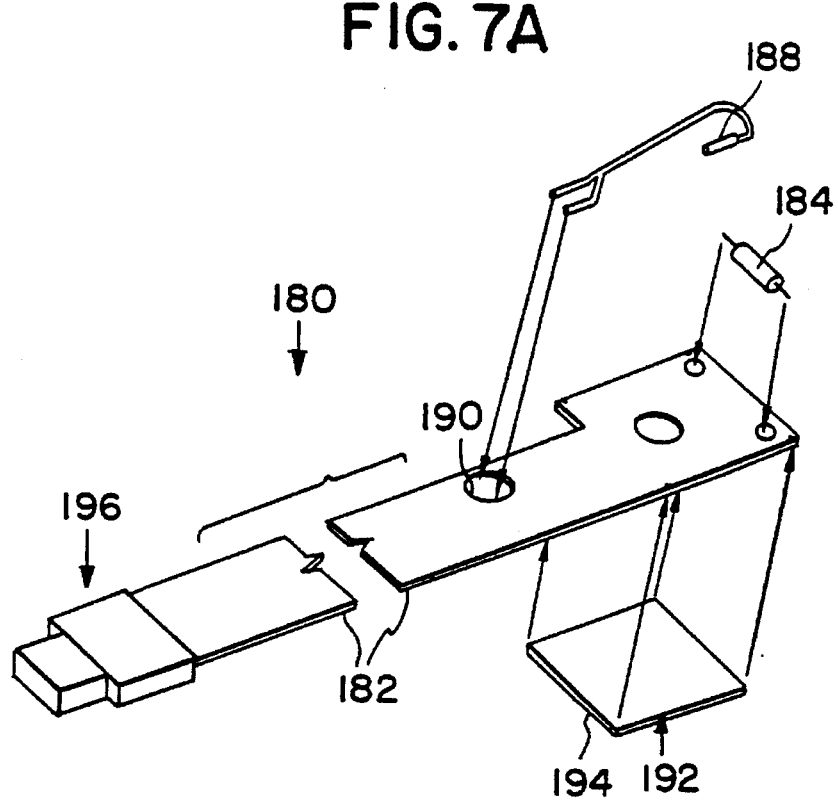
FIGS. 7a–b illustrate an enlarged, fragmentary, exploded perspective view and a fragmentary bottom plan view, respectively, of a detail of FIG. 5.
Figure 7B:
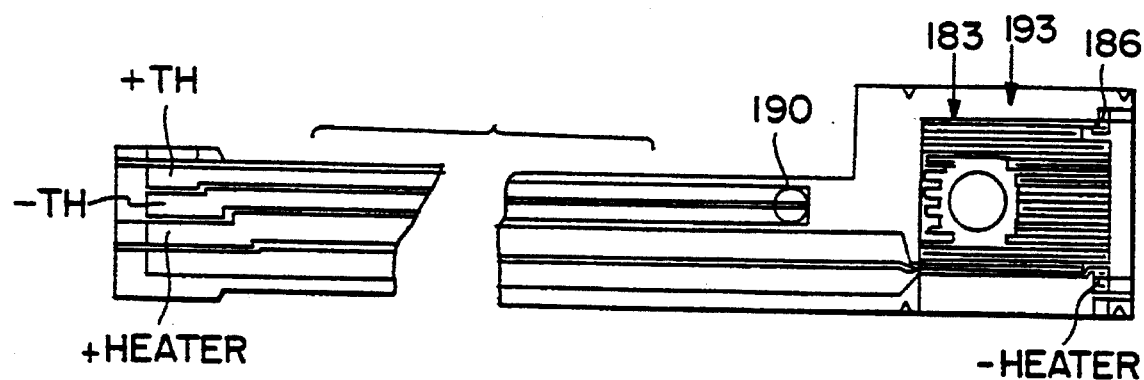
Figure 14:
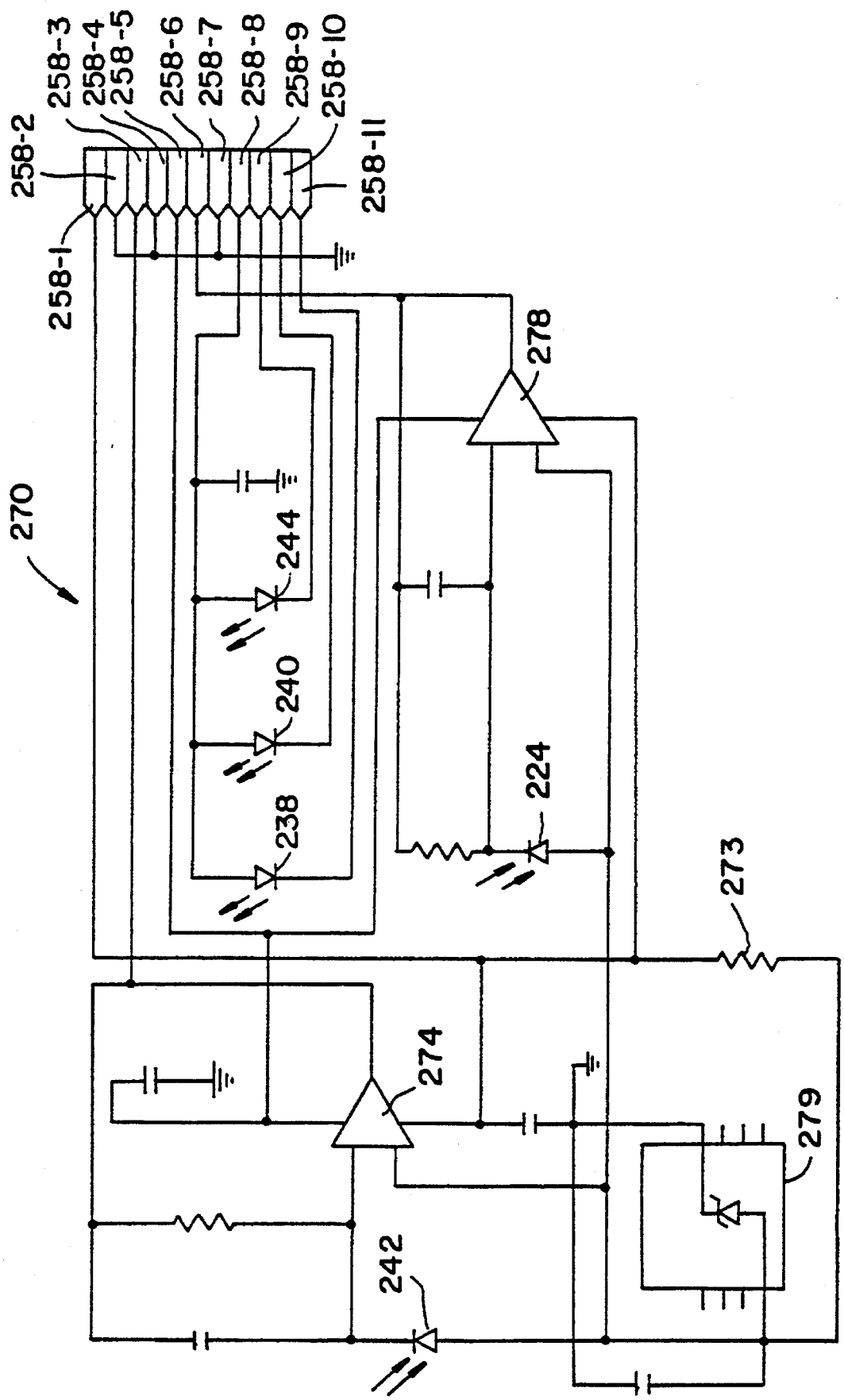
FIG. 14 illustrates a schematic diagram of an electric circuit of the instrument of FIGS. 1 and 13.
Figure 15A:
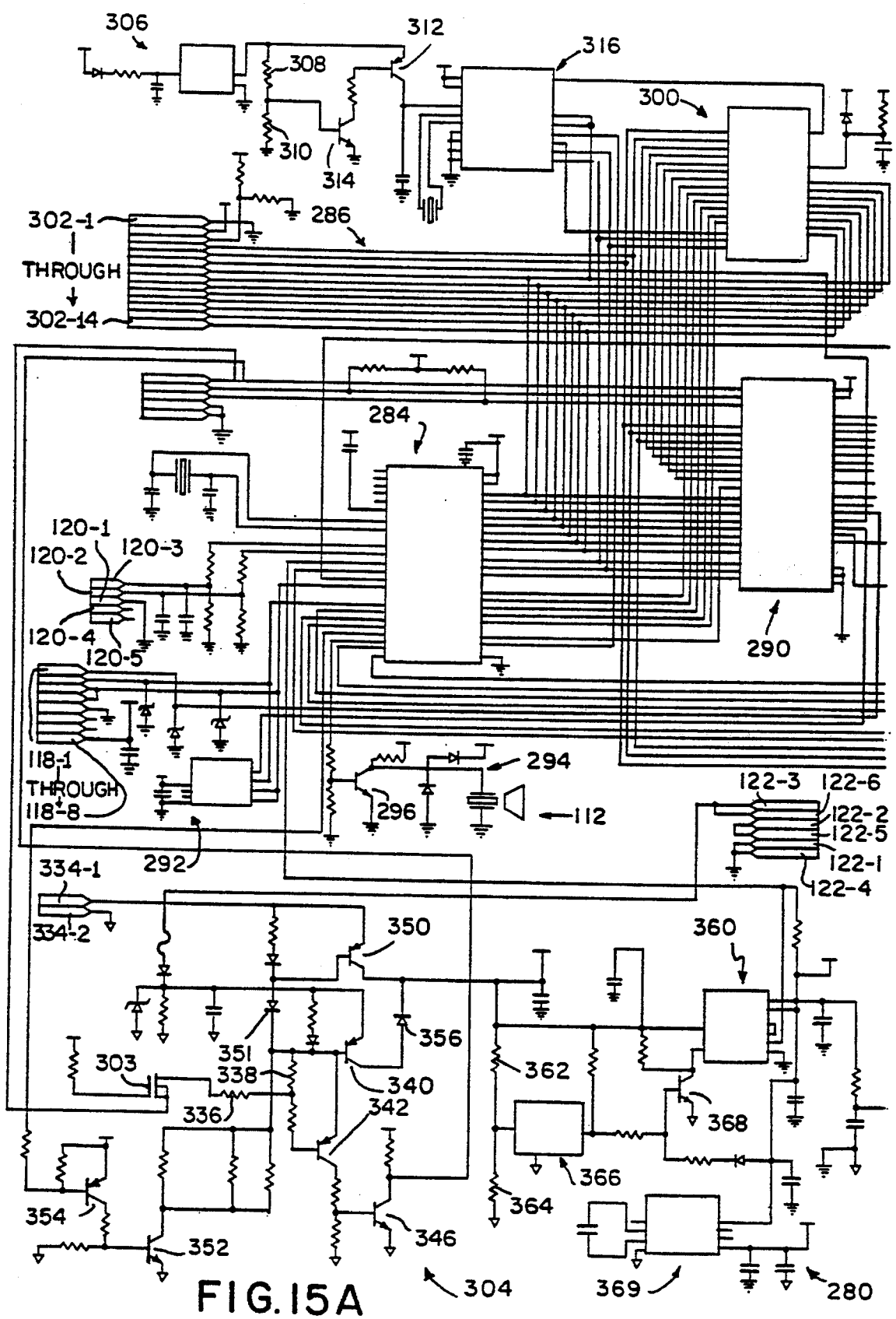
FIGS. 15a–b illustrate a schematic diagram of an electric circuit of the instrument of FIGS. 1 and 13.
Figure 15B:
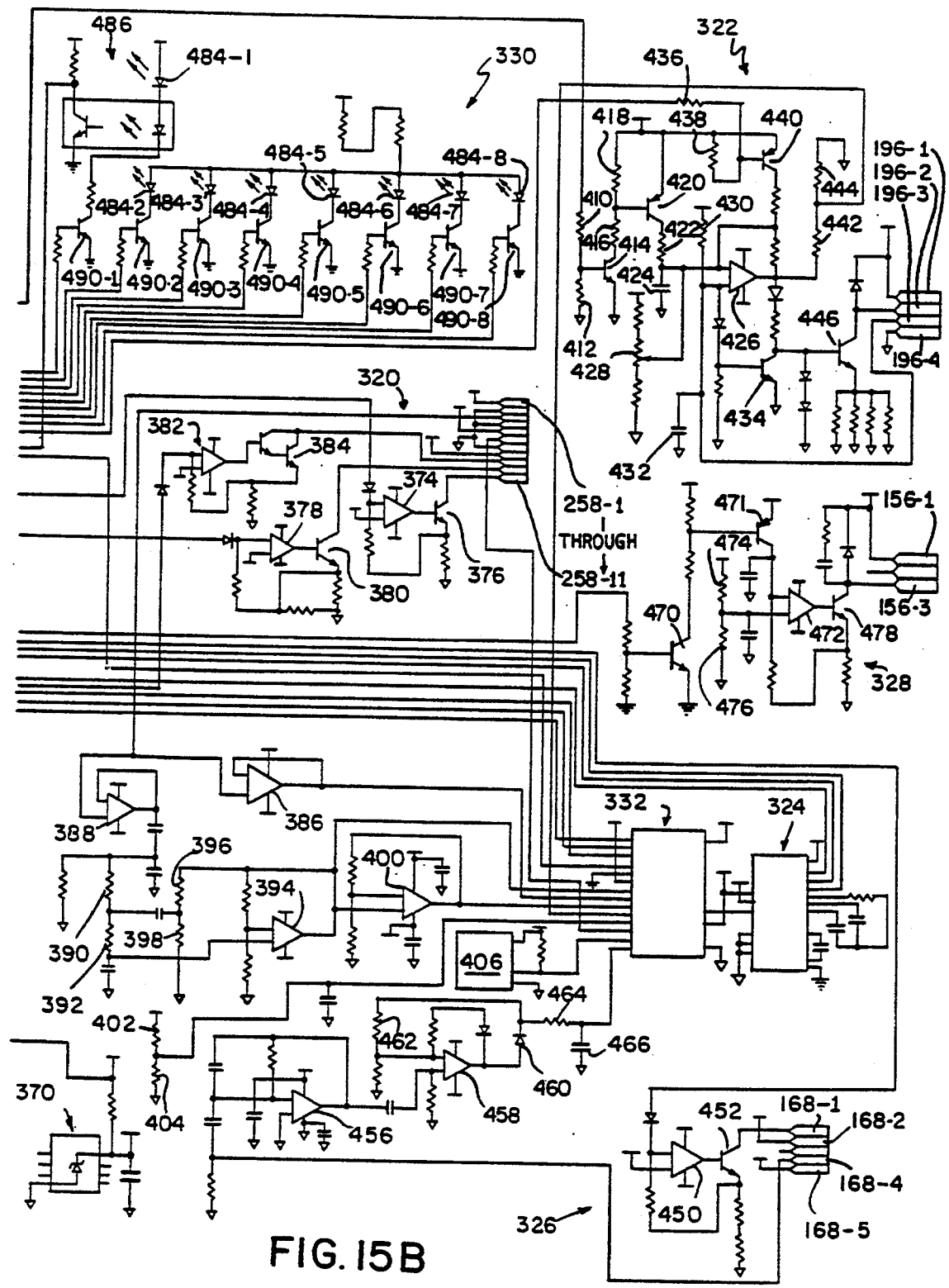
Figure 18:
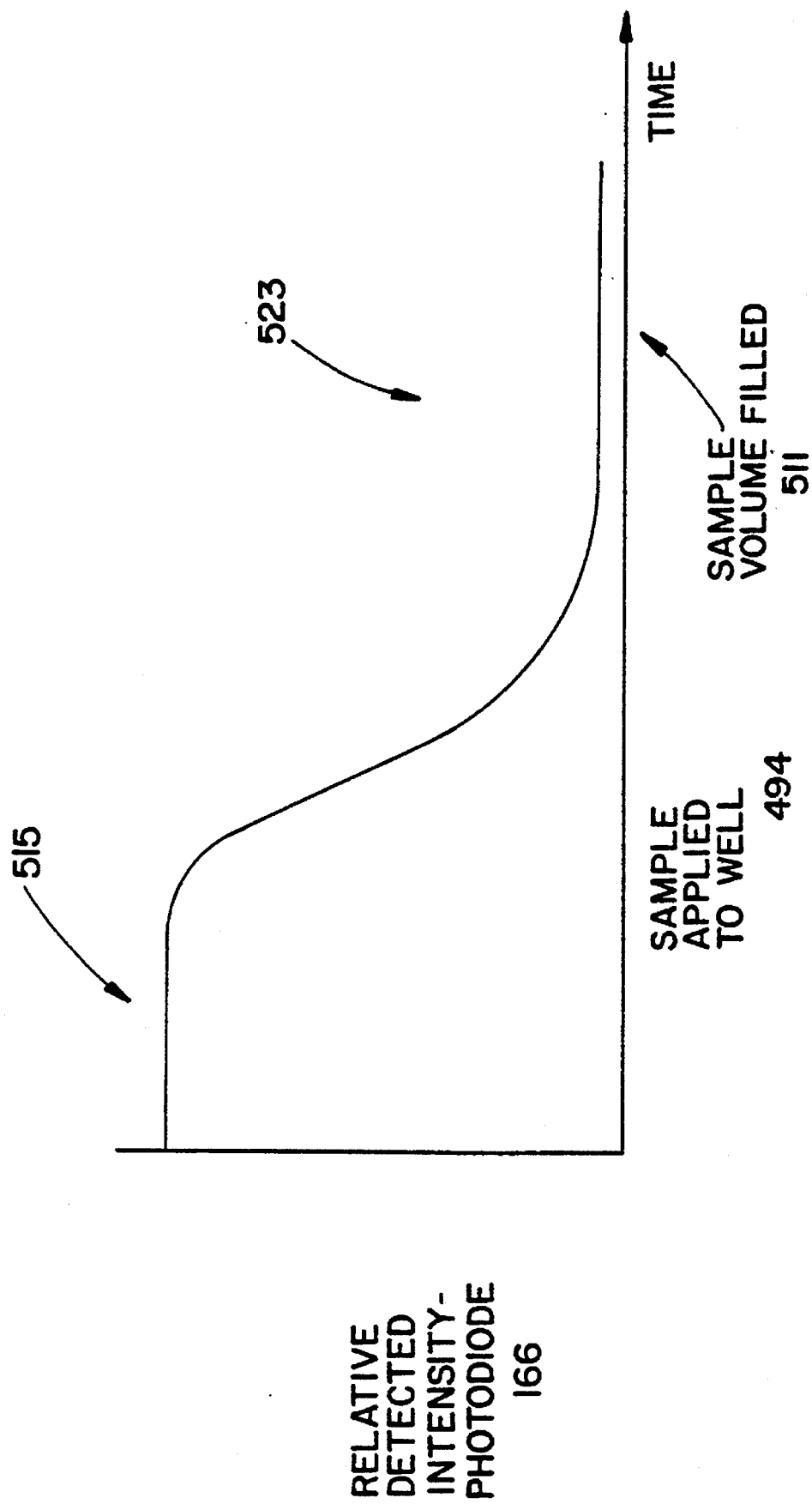
FIG. 18 illustrates a detected light profile according to the present invention.

FIGS. 17a–b are much-enlarged fragmentary longitudinal sectional views of a strip 101 taken along section lines 17—17 of FIG. 4. Generally, in the absence of liquid blood, a blood fraction or control (FIG. 17a), the indices of refraction of the strip bottom 507 and top 509 and the air-filled sample volume 511 between them are such that the level of light from LED 164 returning to photodiode 166 is relatively higher. This is illustrated at region 515 of FIG. 18. A liquid sample 513, be it blood, a blood fraction or a control, is deposited into the sample well 494 of strip 101 and migrates into region 511 of strip 101 over region 211 of instrument 100. Owing generally to the matching of the strip bottom 507's, top 509's and liquid 513's indices of refraction and absorption in the case of clear liquids, and generally to absorption and scattering effects in the case of whole blood, a relatively lower light level is detected by photodiode 166 as illustrated at region 523 in FIG. 18 when a liquid is present on strip 101 adjacent region 211. This optical detection scheme permits a clear control to be used.

Figure 19:
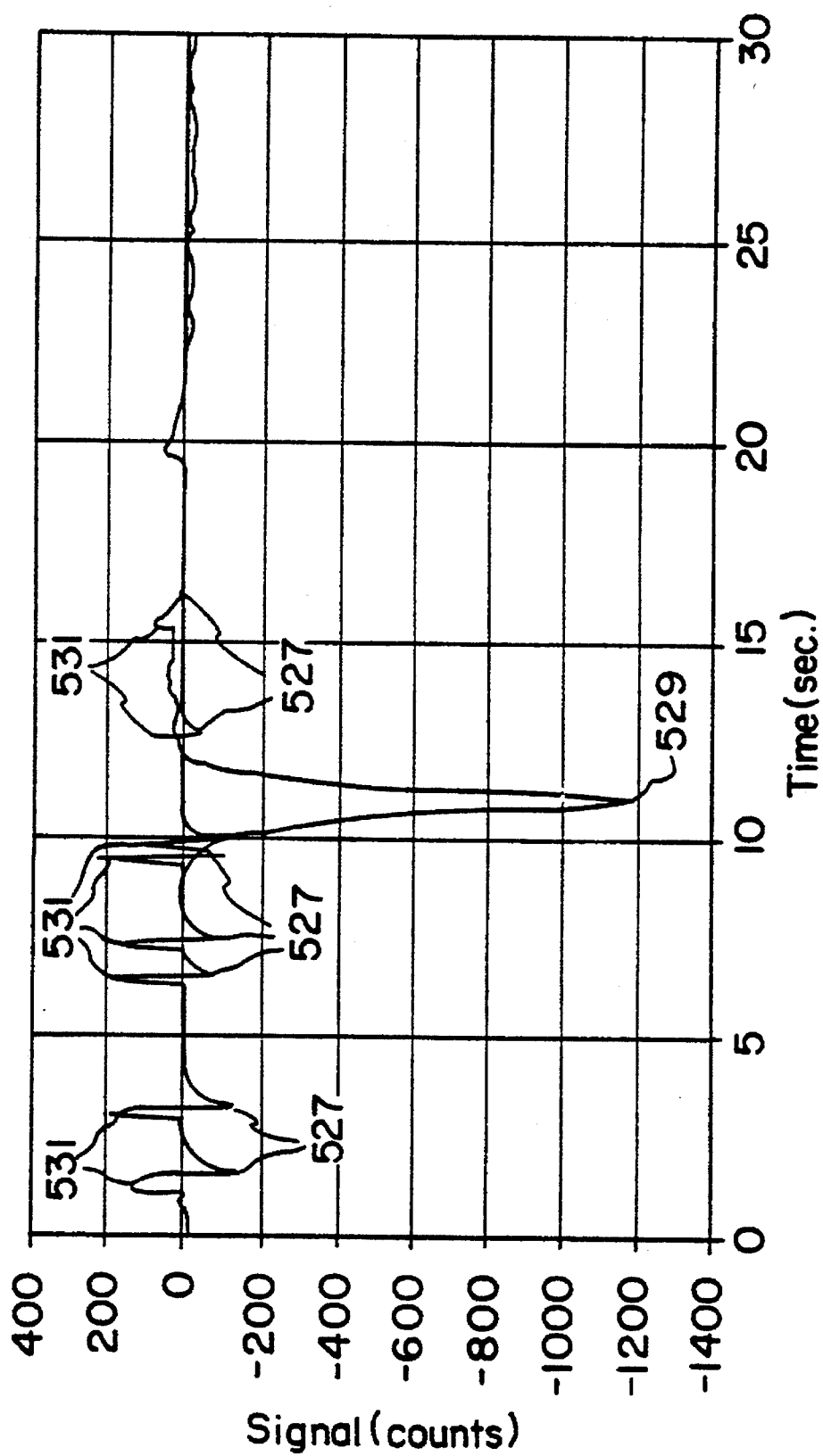
FIG. 19 illustrates two waveforms useful in understanding the start noise immunization technique employed in an instrument according to the present invention.

FIG. 19 illustrates two waveforms useful in understanding the start noise immunization technique employed in an instrument according to the present invention. It has been experimentally determined that, unless provisions are made in instrument 100 to prevent it, instrument 100 can be falsely triggered by negative-going noise spikes 527 that are generated during application of a sample to a test strip 101. Such spikes 527 are caused when the user accidentally taps or moves the strip 101 from side to side or in and out of the optics assembly 116 during sample application. Such negative-going spikes 527 can be greater than the instrument 100's −60 mV starting threshold, but are typically shorter in duration than the negative-going start signal 529 and are preceded or followed immediately by positive-going spikes 531. This is in contrast to the actual liquid sample signal 529 which is only negative-going. This difference is used to discriminate effectively between signal 529 and noise 527, 531. The instrument 100's START algorithm discriminates between short (noise) 527, 531 and long (start signal) 529 duration signals using negative trend, rate of signal change and negative threshold criteria. The flow of the START algorithm includes the following illustrative characteristics: three consecutive data points sampled 50 msec apart must be negative relative to a reference and have rates of signal change more negative than −7.3 mV/50 msec (−30 counts of the A/D converted input signal at 0.243 mV/count) with an absolute signal change more negative than the −60 mV (−246 counts) instrument 100 start threshold. The parameters stored in the EEPROM 119 then would include a signal delta of −30 counts and a start threshold of −246 counts.

μC 284 is programmed to operate the blood coagulation time measuring instrument 100. More particularly, μC 284 is programmed with software for processing the signal corresponding to the characteristic light transmission of the sample or control and for assigning a number to the sample or control equal to the time interval between the mixing of reagents with the sample or control and the polymerization of fibrin, typically referred to as instrumental Prothrombin Time (IPT). μC 284 then provides an output in an accepted clinical scale.

An example of a typical signal corresponding to the characteristic light transmission of the sample is illustrated in FIG. 16. The signal has the electromagnet 140 frequency of about 2 Hz. The relevant part of the signal is a voltage envelope buildup followed by a voltage envelope decay. The voltage envelope buildup is gradual, but definite. The voltage envelope decay is fairly steep for a normal sample, and more gradual and prolonged for an abnormal sample.

The signal typically has a leader which includes a fluctuating offset. After about 8–10 seconds, the signal stabilizes into a signal which is generally symmetrical about the zero voltage level. The stable part of the signal has a minimum peak-to-peak amplitude of at least 250 mV. The stable part of the signal has a gradual rise followed by a decay of at least 60 mV. Instrument 100 starts a clock at the moment the sample enters the MAIN assay area. The time between the start of the clock and the first synchronization pulse from the electromagnet 140 is stored by µC 284 as the offset time. Alternating voltage peaks are converted to digital values and stored. µC 284 stores the signal peaks in a buffer for 75 seconds. The sampling frequency is 2 Hz. The tail of the signal should be no greater than about 0.75 times the maximum peak of the stable portion of the signal.

Figure 20A:
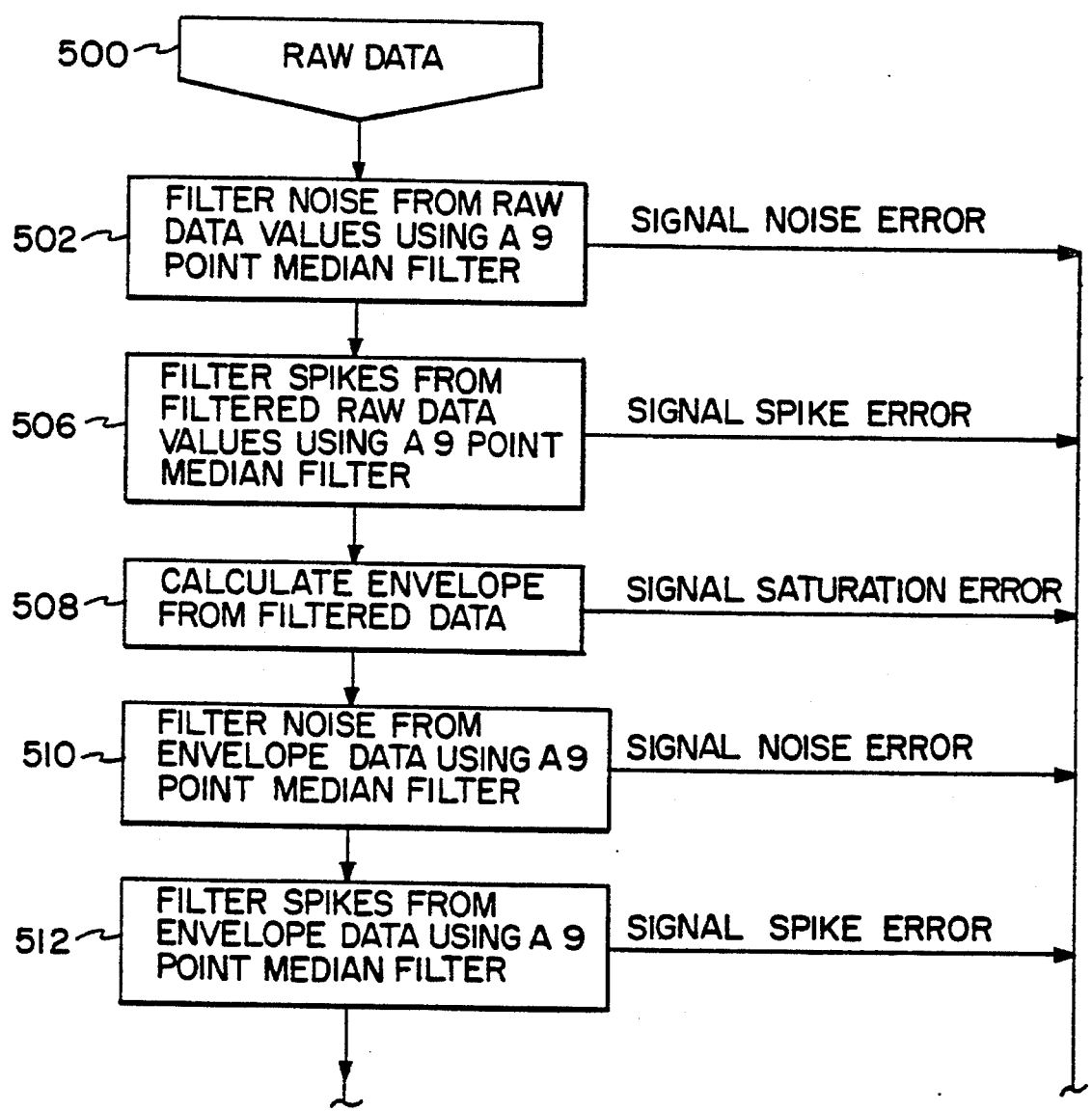
FIG. 20 is a flow diagram illustrating the steps performed by an instrument according to the present invention to process the signal of FIG. 16; and, FIGS. 21–28 illustrate in greater detail portions of the flow diagram illustrated in FIG. 20.
Figure 20B:
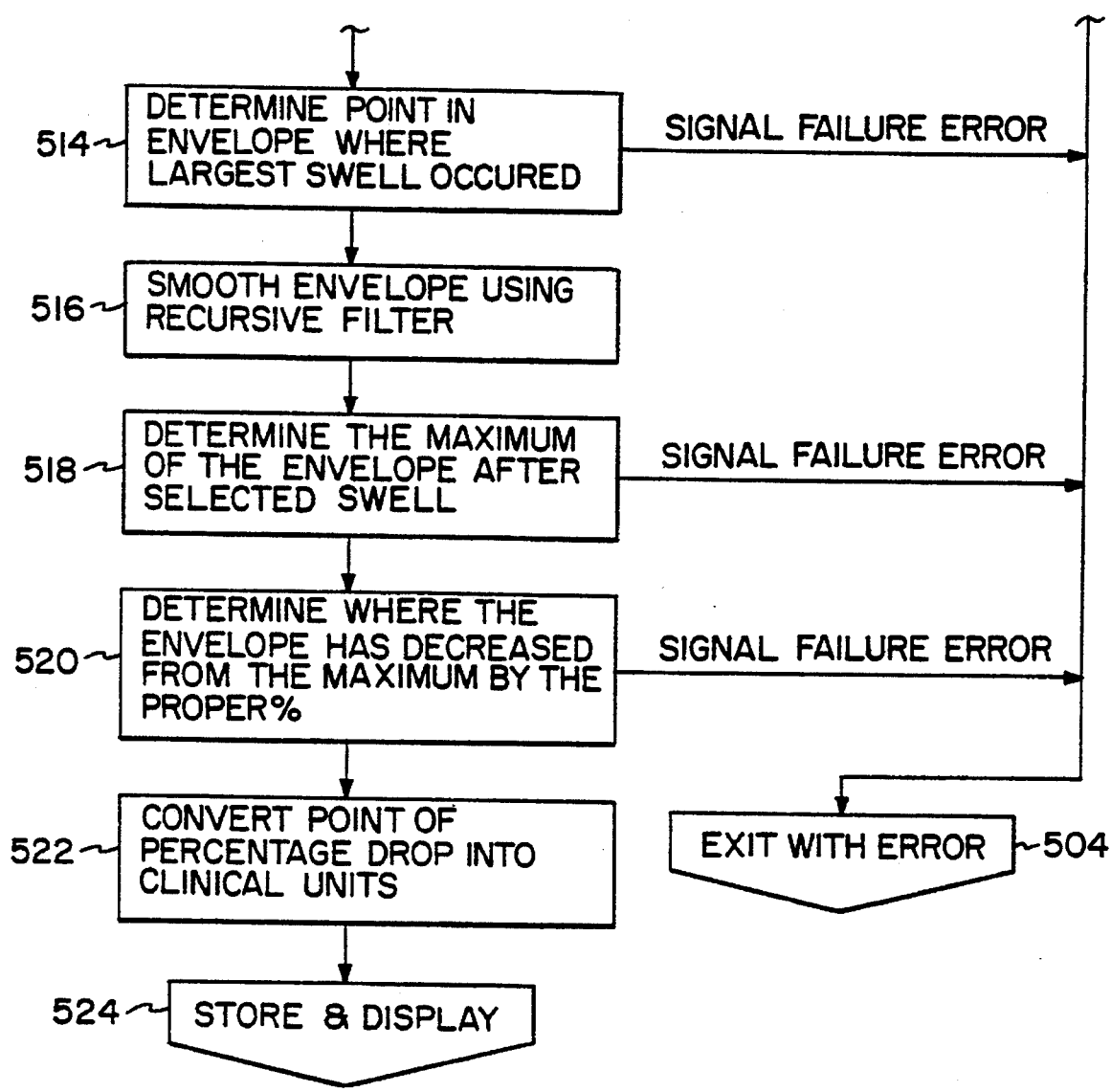

Once the entire signal from the sample is stored in the buffer by µC 284, µC 284 processes the signal to detect the IPT for the sample and to provide a desired output. FIGS. 20–28 illustrate the steps performed by µC 284 for processing the stored signal data. FIG. 20 broadly illustrates the steps for processing the signal, and FIGS. 21–28 illustrate the various function blocks of FIG. 20 in more detail.

As illustrated in FIG. 20, raw data related to the signal illustrated in FIG. 16 is collected and stored as discussed above. This step is illustrated at block 500. Stored data includes an alternating series of positive and negative peak values corresponding to the positive and negative peaks from the signal illustrated in FIG. 16. Noise is then filtered from the stored raw data values using a 9 point median filter as illustrated at block 502. If a signal noise error is detected, µC 284 exits from the main processing program and generates an error signal as illustrated at block 504. After the stored data is noise filtered at block 502, µC 284 filters the stored data to remove voltage spikes using a 9 point median filter as illustrated at block 506. If a signal spike error is detected, µC 284 exits the main processing program and generates an error signal at block 504. If a signal spike error is not detected at block 506, µC 284 calculates the signal envelope from the filtered data at block 508. If a signal saturation error is detected, µC 284 exits the main processing program and generates an error signal at block 504. After the signal envelope is calculated at block 508, µC 284 filters noise from the envelope using a 9 point median filter as illustrated at block 510. If a signal noise error is detected, µC 284 exits the main processing program and generates an error signal at block 504. After noise is filtered from the envelope at block 510, µC 284 again filters spikes from the envelope using a 9 point median filter as illustrated at block 512. If a signal spike error is detected, µC 284 exits the main processing program and generates an error signal at block 504.

µC 284 next determines the point in the stored envelope where the largest swell occurred at block 514. If a signal failure error is detected, µC 284 exits the main processing program and generates an error signal at block 504. µC 284 then smooths the envelope using a recursive filter as illustrated at block 516. Next, µC 284 determines the maximum value of the envelope at a point after the selected swell at block 518. If a signal failure error is detected, µC 284 exits the main processing program and generates an error signal at block 504. µC 284 then determines the time at which the envelope has decreased by a predetermined percentage from the maximum value as illustrated at block 520. This time establishes the IPT for the sample or control. Illustratively, the predetermined percentage for instrument 100 is 5.078%. If a signal failure error is detected, µC 284 exits the main processing program and generates an error signal at block 504. µC 284 then converts the detected IPT into desired clinical units using stored tables for comparison as illustrated at block 522. Finally, µC 284 stores and displays the value of the sample or control as illustrated at block 524.

Figure 21A:
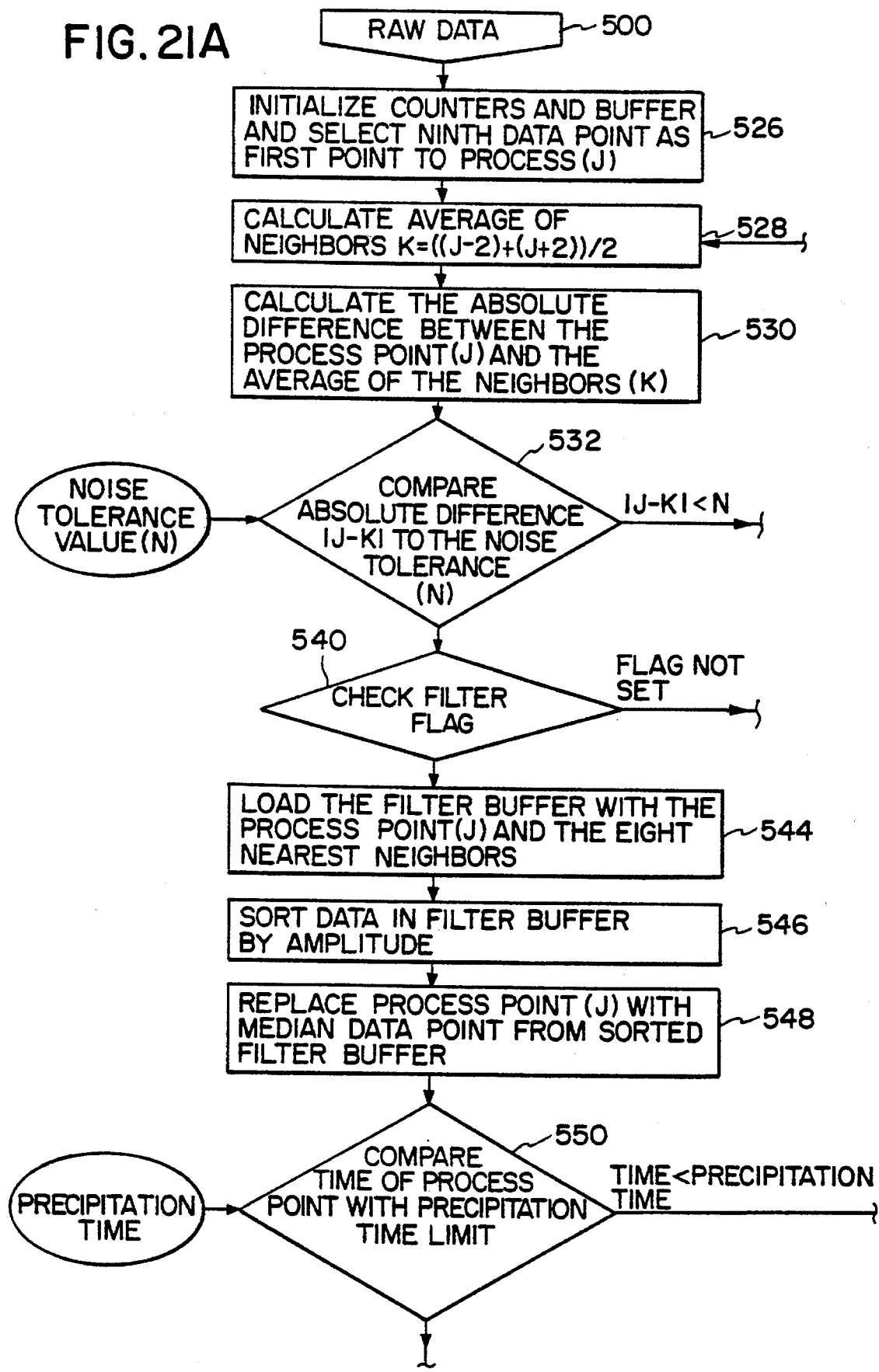
Figure 21B:
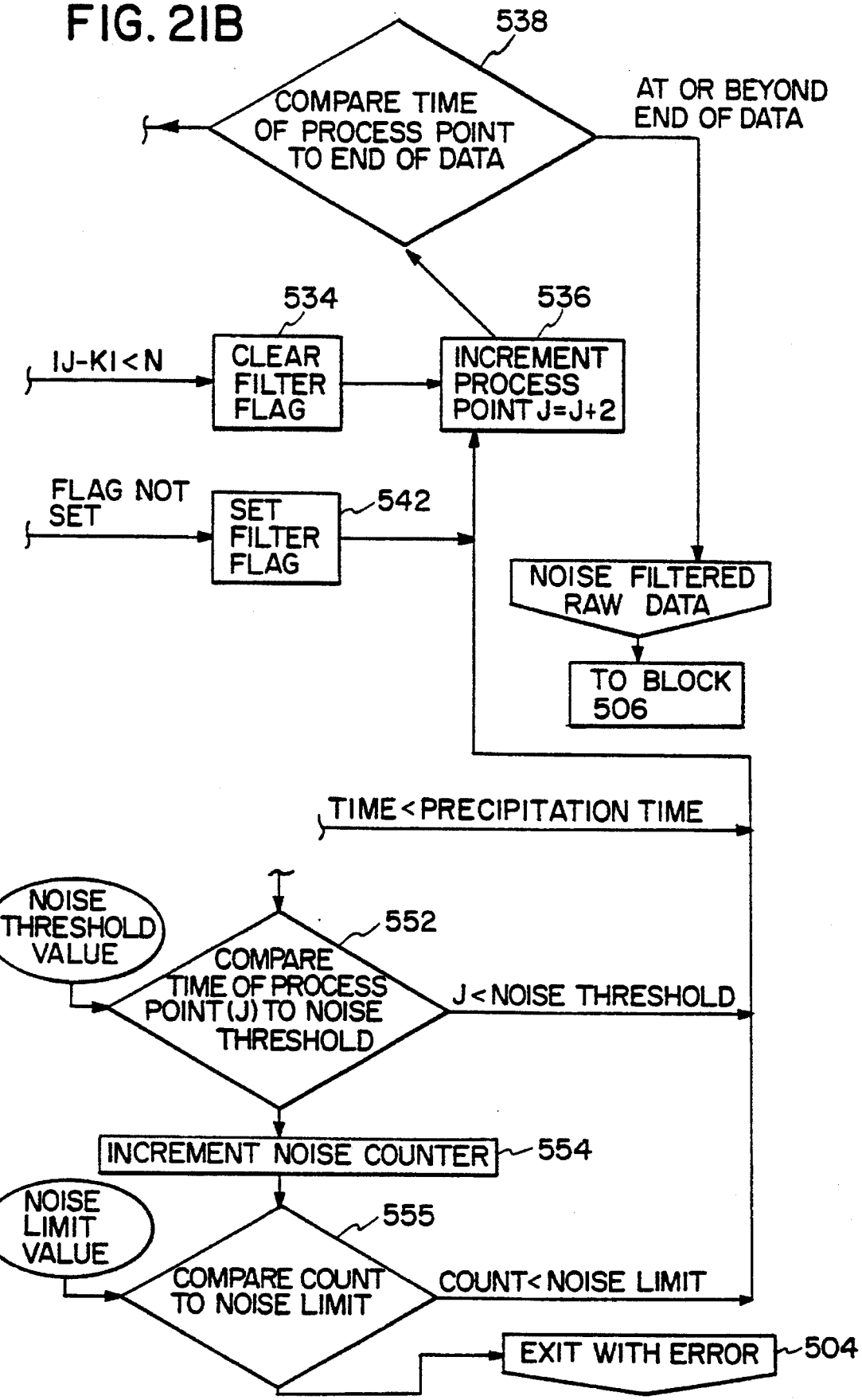

Details of the step of filtering noise from the stored raw data values at block 502 are illustrated in FIG. 21. At this point in the data processing, the stored values include positive values and negative values stored at every other memory location. Therefore, during the filtering steps at blocks 502 and 506, two passes over the stored data are made. The first filtering pass is made to filter the positive stored values, and the second filtering pass is made to filter the negative stored values. µC 284 first initializes counters and the storage buffer and selects the ninth stored data point as the first process point j as illustrated at block 526. µC 284 then calculates the average value k of the two nearest neighbors of process point j using the equation k = (value at point (j−2)+value at point (j+2))/2 as illustrated at block 528. Next, µC 284 calculates the absolute difference between the process point j and the average k of its neighbors at block 530. µC 284 then compares the calculated absolute difference to a preset noise tolerance percentage value n as illustrated at block 532. The noise tolerance percentage value n is a parameter stored in key 119 as an integer. The noise tolerance percentage value can have values ranging from 1 to 255, and is used to flag outlying data points during the filtering stages illustrated in blocks 502, 506, 510, and 512 of FIG. 20. In the illustrated embodiment, the stored value for the noise tolerance percentage value n in key 119 is 13. Therefore, the noise tolerance percentage is 5.078% (0.3906%×13). A filter flag is set if the difference between the process point j and the average k of the neighbors is greater than the noise tolerance percentage value n. As discussed below, in blocks 510 and 512, the value for the noise tolerance percentage is doubled since a rectified signal envelope having about twice the magnitude of the non-rectified signal is filtered at blocks 510 and 512.

The purpose of the filter flag is so that only process points containing noise are filtered. When noise occurs at a particular process point, the noise point will first affect the average of the neighbors of the preceding process point. Therefore, the noise point will cause the average k to exceed process point j by more than the noise tolerance percentage value n. Only one filter flag is used by µC 284.

If the absolute difference calculated at block 530 is less than the noise tolerance percentage value n, µC 284 clears the filter flag as illustrated at block 534. µC 284 then increments process point j by setting j=j+2 as illustrated at block 536. µC 284 then compares the time of the process point j to the end of data location as illustrated at block 538. If the new process point j is at or beyond the storage location of the end of the stored data, µC 284 proceeds to block 506 of FIG. 20. If the process point is not at or beyond the end of the data, µC 284 returns to block 528 to calculate the average value of the neighbors for the new process point j.

If the absolute difference calculated at block 530 is greater than the preset noise tolerance percentage value, µC 284 checks the filter flag at block 540. If the filter flag is not set, this indicates that the noise is caused by a process point (j+2) affecting the average k. Therefore, µC 284 does not filter the present process point j. µC 284 sets the filter flag at block 542 and then proceeds to increment process point j at block 536.

If the filter flag is set at block 540, μC 284 determines that the current process point j is a noise point since it affected the average for the preceding process point (j−2) and caused the filter flag to be set in the preceding pass of the filter. Therefore, μC 284 filters the detected noise process point j only when the filter flag is already set.

In order to filter process point j, μC 284 loads the filter buffer with process point j and its eight nearest neighbors (j−8), (j−6), (j−4), (j−2), (j+2), (j+4), (j+6), and (j+8) as illustrated at block 544. Data stored in the filter buffer is then sorted by amplitude as illustrated at block 546. Process point j is then replaced with the median data point from the sorted filter buffer at block 548.

The time of process point j is then compared to a preset precipitation time limit at block 550. The precipitation time limit is stored as an integer in key 119 and has a value ranging between 1 and 255. Noise found in the signal at or before the preset precipitation time limit is not used in the determination of the quality of the signal. Illustratively, the precipitation time limit value is set at 10 seconds. The resolution for the stored precipitation time limit is 0.25 seconds. Therefore, the integer value 40 (10 sec. ×4 samples per second) is stored in key 119. If the time of process point j is less than the precipitation time limit, μC 284 increments process point j at block 536. If the time of process point j is greater than the precipitation time limit, μC 284 compares the replaced value of process point j to a noise threshold value at block 552. Illustratively, the noise threshold value is 74.95 mV. The noise threshold value is used during the filtering stages to qualify the filtered data as a "significant" noise point. If the absolute magnitude of the filtered data point is above the preset noise threshold value, then the data is considered to be a significant noise point.

The determination that a data point had significant noise is not based on the amount of noise of that data point, but where in the signal that the noise occurred. A noise point occurring in that part of the signal where voltage levels are below this threshold voltage is considered insignificant because the noise did not occur in a relevant part of the signal which will be used to calculate IPT.

If the absolute voltage magnitude of process point j is less than the preset noise threshold value at block 552, μC 284 determines that the noise point is not significant, proceeds to block 536, and increments process point j. If the absolute magnitude of the process point is greater than the noise threshold value at block 552, μC 284 increments a noise counter at block 554. μC 284 then compares the noise counter value to a preset noise limit value at block 555. Illustratively, the noise limit value has a value of 10 for each full pass over the entire signal including both the top and bottom portions of the signal. If the actual count of significant noise points is less than or equal to the noise limit value, μC 284 advances to block 536 and increments process point j. If the actual count of significant noise points is greater than the noise limit, μC 284 exits the main processing program and generates an error signal at block 504.

Figure 22A:
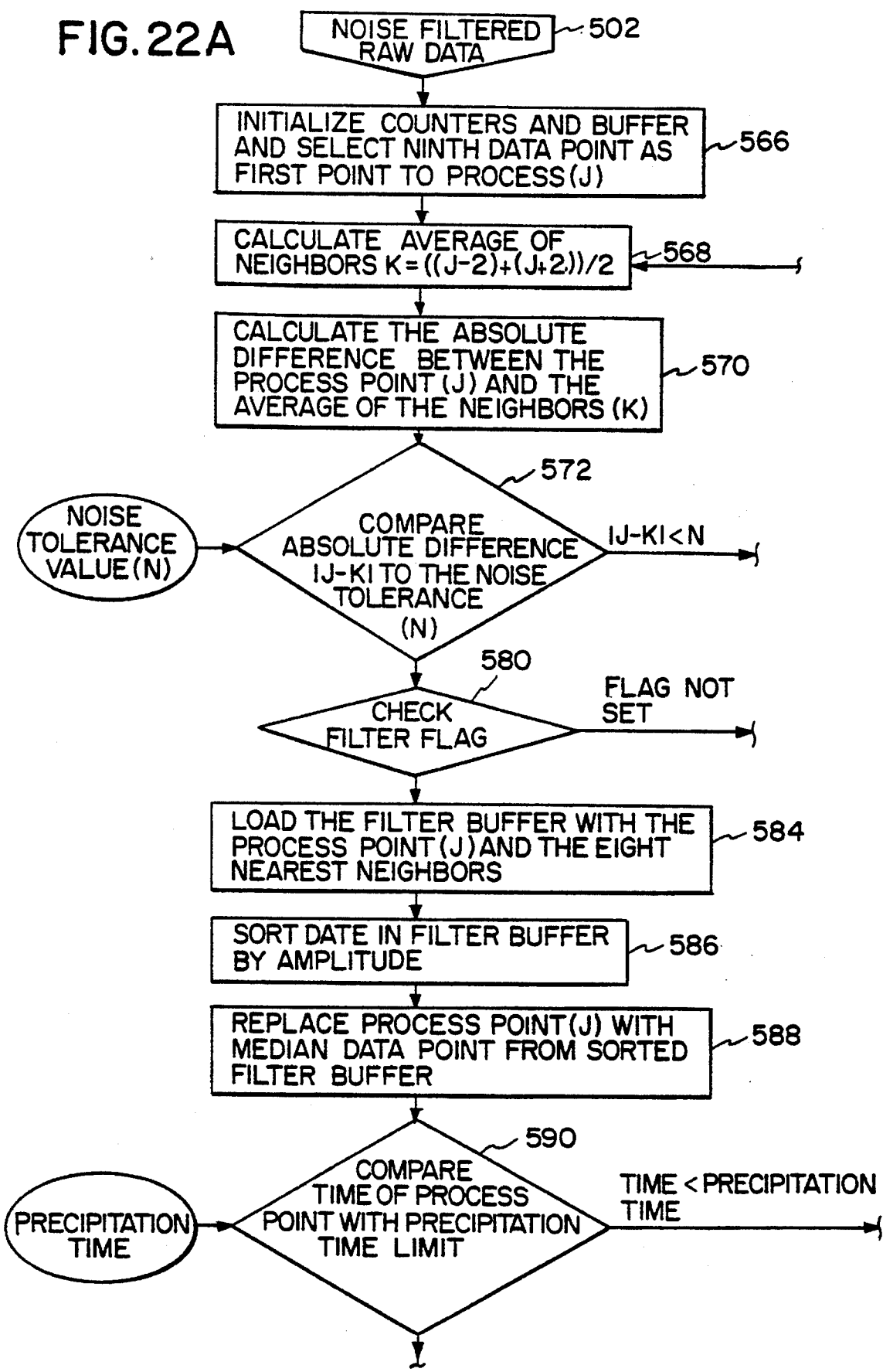

FIG. 22 is an expanded flow chart illustrating the steps performed by μC 284 at block 506. μC 284 first initializes counters and the storage buffer and selects the ninth stored data point as the first process point j as illustrated at block 566. μC 284 then calculates the average value k of the two nearest neighbors of process point j using the equation k= (value at point (j−2)+value at point (j+2))/2 as illustrated at block 568. Next, μC 284 calculates the absolute difference between the process point j and the average k of its neighbors at block 570. μC 284 then compares the calculated absolute difference to a preset noise tolerance percentage value n as illustrated at block 572. Illustratively, the noise tolerance percentage value n is 13. Therefore, the noise tolerance percentage is 5.078% (0.3906%×13).

If the absolute difference calculated at block 570 is less than the noise tolerance percentage value n, μC 284 clears the filter flag as illustrated at block 574. μC 284 then increments process point j by setting j=j+2 as illustrated at block 576. μC 284 then compares the time of the process point j to the end of data location as illustrated at block 578. If the new process point j is at or beyond the storage location of the end of the stored data, μC 284 proceeds to block 508 of FIG. 20. If the process point is not at or beyond the end of the data, μC 284 returns to block 568 to calculate the average value of the neighbors for the new process point j.

If the absolute difference calculated at block 570 is greater than the preset noise tolerance percentage value, μC 284 checks the filter flag at block 580. If the filter flag is not set, this indicates that the noise is caused by a process point (j+2) affecting the average k. Therefore, μC 284 does not filter the present process point j. μC 284 sets the filter flag at block 582 and then proceeds to increment process point j at block 576.

If the filter flag is set at block 580, μC 284 determines that the current process point j is a noise point since it affected the average for the preceding process point (j−2) and caused the filter flag to be set in the preceding pass of the filter. Therefore, μC 284 filters the detected noise process point j only when the filter flag is already set.

In order to filter process point j, μC 284 loads the filter buffer with process point j and its eight nearest neighbors (j−8), (j−6), (j−4), (j−2), (j+2), (j+4), (j+6), and (j+8) as illustrated at block 584. Data stored in the filter buffer is then sorted by amplitude as illustrated at block 586. Process point j is then replaced with the median data point from the sorted filter buffer at block 588.

The time of process point j is then compared to a preset precipitation time limit at block 590. The precipitation time limit is illustratively set at 10 seconds. If the time of process point j is less than the precipitation time limit, μC 284 increments process point j at block 576. If the time of process point j is greater than the precipitation time limit, μC 284 compares the replaced value of process point j to a noise threshold value at block 592. Illustratively, the noise threshold value is 74.95 mV.

If the absolute voltage magnitude of process point j is less than the preset noise threshold value at block 592, μC 284 determines that the noise point is not significant, proceeds to block 576, and increments process point j. If the absolute magnitude of the process point is greater than the noise threshold value at block 592, μC 284 exits the main processing program and generates an error signal at block 504.

Figure 23:
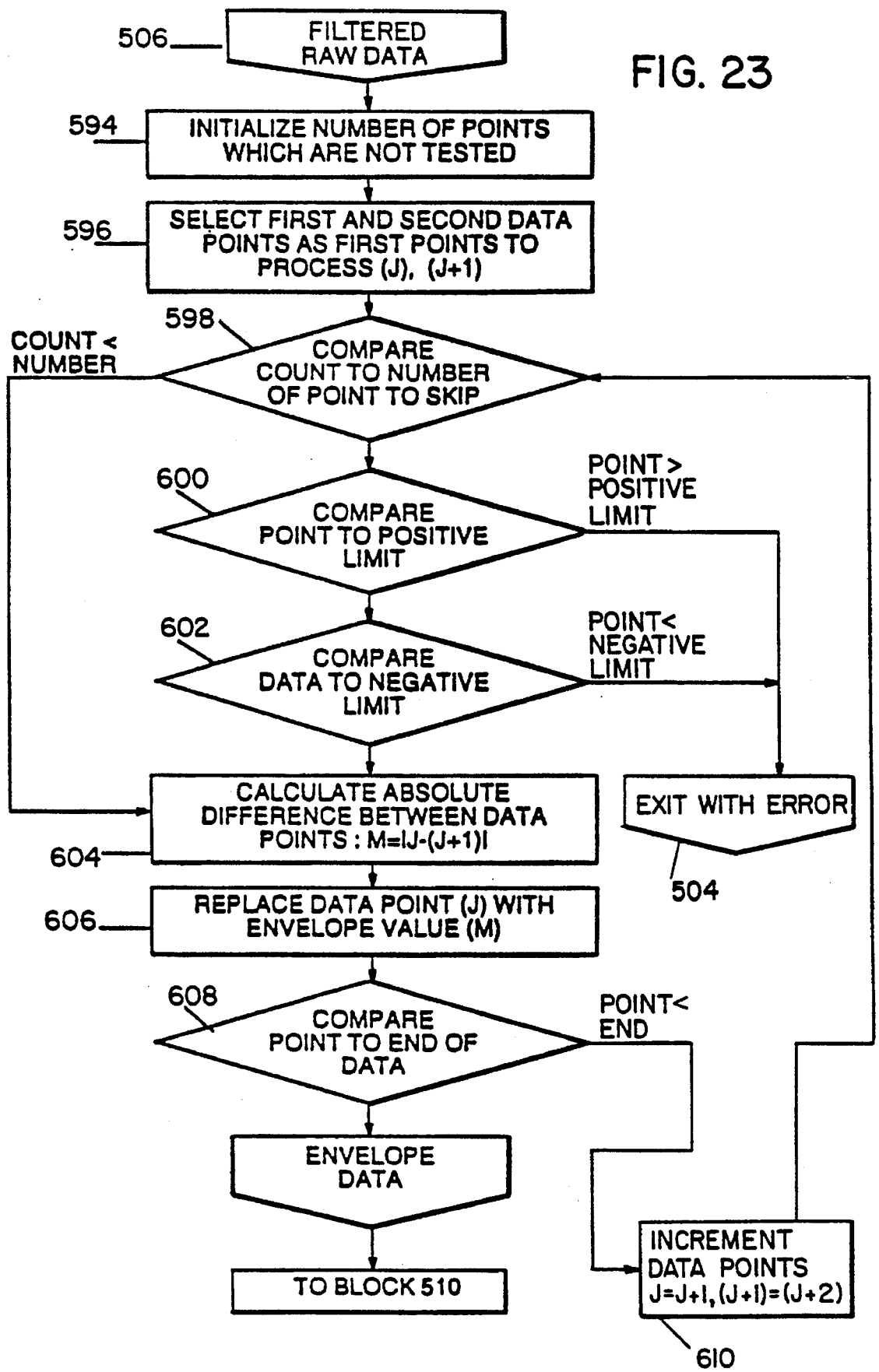

FIG. 23 is a flow chart illustrating the steps performed by μC 284 to calculate the envelope from filtered data at block 508 of FIG. 20. From block 506, μC 284 initializes the number of data points which are not tested at block 594. Typically, a selected number of data points are ignored since these data points may be affected by outside influences, such as turning on MAIN assay LED 244. Preferably, the first two data points from the filtered raw data are ignored. μC 284 then selects the first and second data points to be processed at block 596. In this instance, the first process point is j and the second process point is (j+1). Since μC 284 rectifies the entire signal, both positive and negative data values are used.

μC 284 compares the count to the preset number of points to skip at block 598. If the count is less than the number of points to skip at block 598, μC 284 advances directly to block 604. If the count is greater than the number of points to skip, μC 284 determines whether or not the system is saturated. μC 284 first compares the positive voltage process point to the positive voltage limit at block 600. If the point is greater than the positive limit, μC 284 exits from the main processing program and generates an error signal at block 504. Illustratively, the positive voltage limit is set at 3.9375 V. If the point is less than the positive limit at block 600, μC 284 compares the negative data point to the negative voltage limit at block 602. If the data point is less than the negative limit, μC 284 exits the main processing program and generates an error signal at block 504. Illustratively, the negative voltage limit is −3.9375 V.

If the data point is greater than the negative limit, μC 284 calculates the absolute difference between the first and second data points at block 604. μC 284 then replaces the first data point j with the envelope value m as illustrated at block 606. μC 284 then compares the point to the end of data at block 608. If the point is less than the end of the data, μC 284 increments the data points by setting j=j+1 and by setting (j+1)=(j+2) as illustrated at block 610. μC 284 then advances to block 598. If the point is greater than the end of the data at block 608, then the envelope data has been established and μC 284 advances to block 510.

Figure 24A:
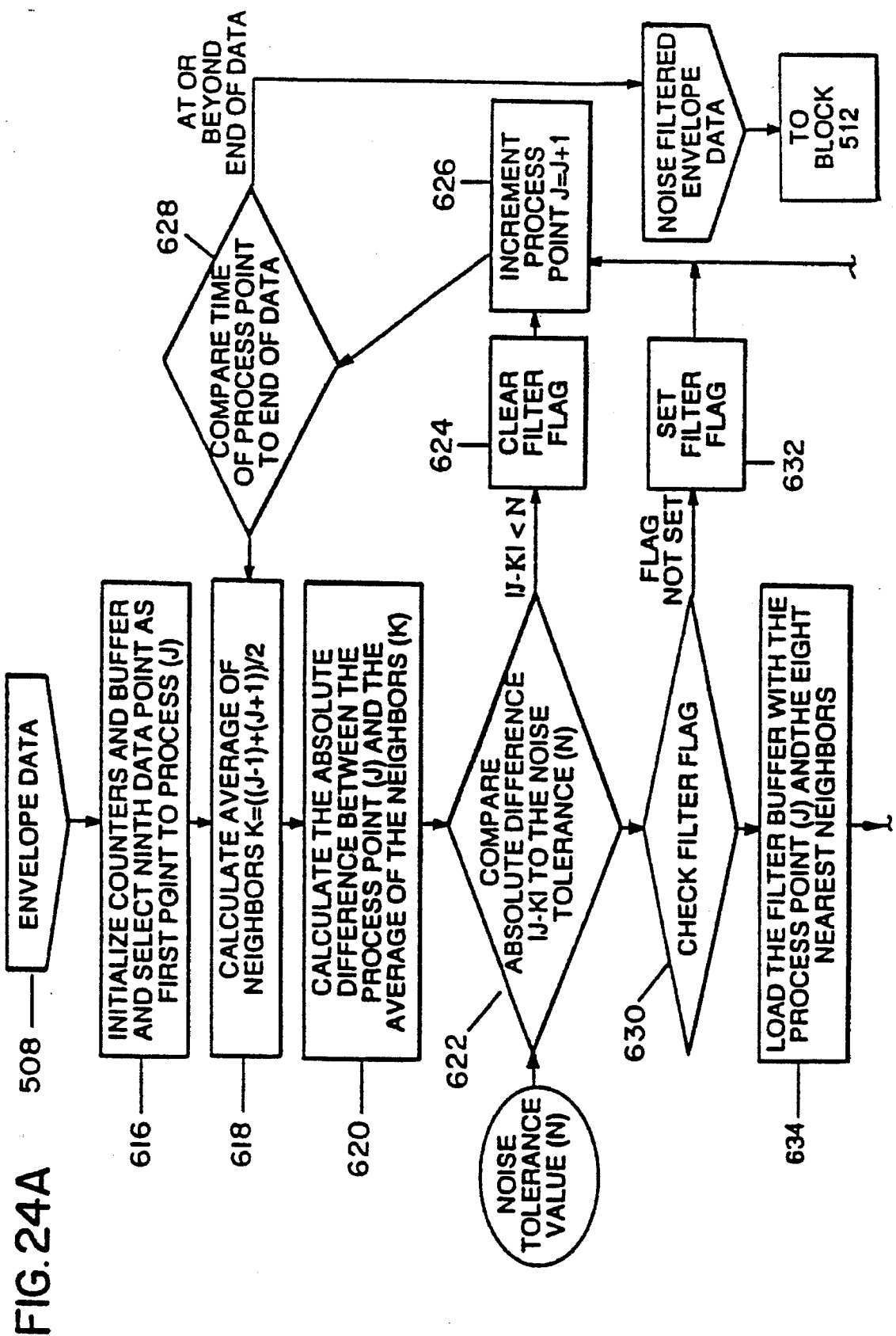
Figure 24B:
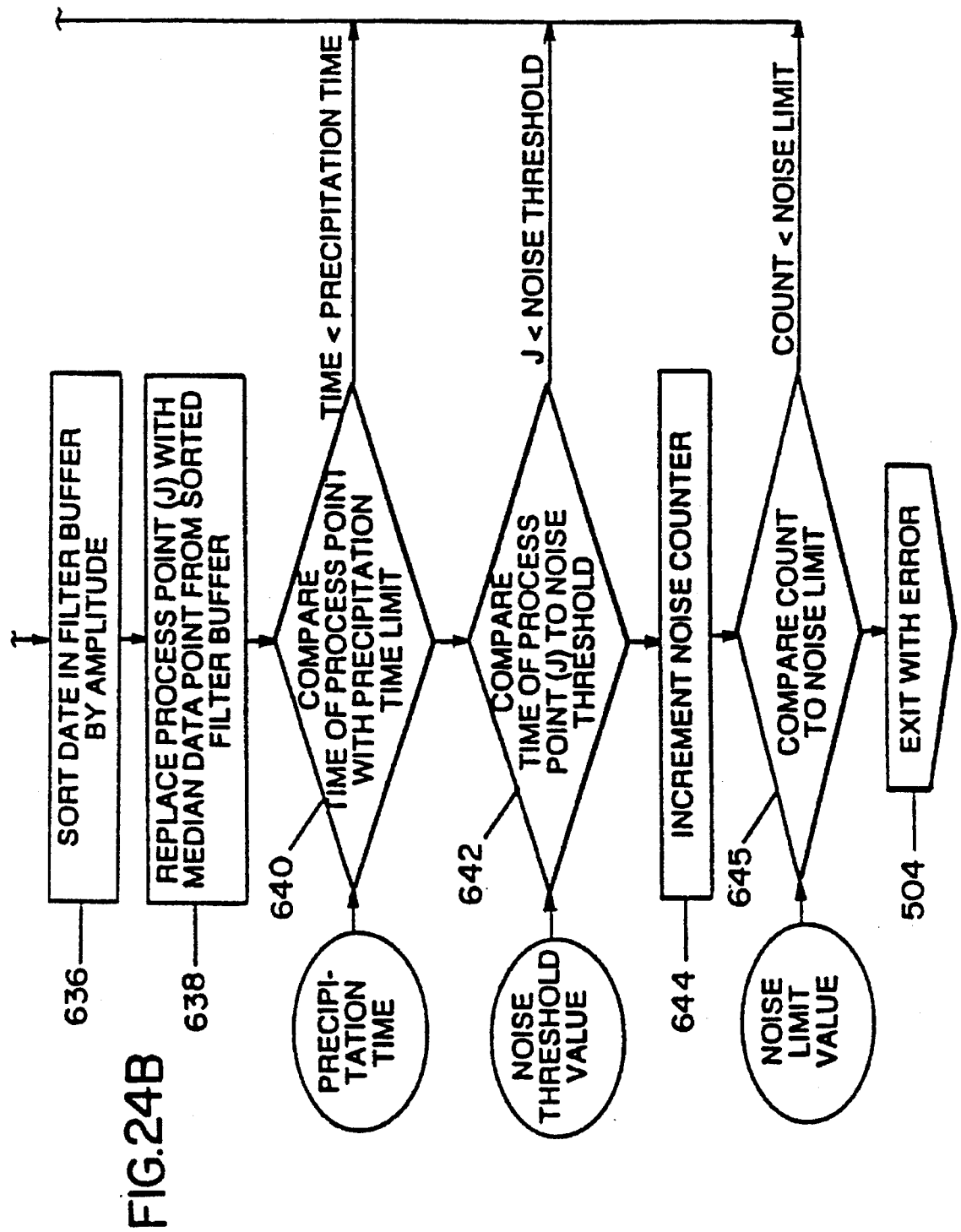

Details of the step of filtering noise from the envelope data values at block 510 are illustrated in FIG. 24. At this point in the data processing, the stored values include only positive values of the envelope stored at every data point. Therefore, during the filtering steps at blocks 510 and 512, only one filtering pass is required. μC 284 first initializes counters and the storage buffer and selects the ninth stored data point as the first process point j as illustrated at block 616. μC 284 then calculates the average value k of the two nearest neighbors of process point j using the equation k=(value at point (j−1)+value at point (j+1))/2 as illustrated at block 618. Next, μC 284 calculates the absolute difference between the process point j and the average k of its neighbors at block 620. μC 284 then compares the calculated absolute difference to a preset noise tolerance percentage value n as illustrated at block 622. The noise tolerance percentage value is doubled in blocks 510 and 512 since a rectified signal envelope having about twice the magnitude of the non-rectified signal is filtered at blocks 510 and 512. In the illustrated embodiment, the stored value for the noise tolerance percentage value n for blocks 510 and 512 in key 119 is 26. Therefore, the noise tolerance percentage is 10.156% (0.3906%×26). A filter flag is set if the difference between the process point j and the average k of the neighbors is greater than the noise tolerance percentage value n.

If the absolute difference calculated at block 620 is less than the noise tolerance percentage value n, μC 284 clears the filter flag as illustrated at block 624. μC 284 then increments process point j by setting j=j+1 as illustrated at block 626. μC 284 then compares the time of the process point j to the end of data location as illustrated at block 628. If the new process point j is at or beyond the storage location of the end of the stored data, μC 284 proceeds to block 512 of FIG. 20. If the process point is not at or beyond the end of the data, μC 284 returns to block 618 to calculate the average value of the neighbors for the new process point j.

If the absolute difference calculated at block 620 is greater than the preset noise tolerance percentage value, μC 284 checks the filter flag at block 630. If the filter flag is not set, this indicates that the noise is caused by a process point (j+1) affecting the average k. Therefore, μC 284 does not filter the present process point j. μC 284 sets the filter flag at block 632 and then proceeds to increment process point j at block 626.

If the filter flag is set at block 630, μC 284 determines that the current process point j is a noise point since it affected the average for the preceding process point (j−1) and caused the filter flag to be set in the preceding pass of the filter. Therefore, μC 284 filters the detected noise process point j only when the filter flag is already set.

In order to filter process point j, μC 284 loads the filter buffer with process point j and its eight nearest neighbors (j−4), (j−3), (j−2), (j−1), (j+1), (j+2), (j+3), and (j+4) as illustrated at block 634. Data stored in the filter buffer is then sorted by amplitude as illustrated at block 636. Process point j is then replaced with the median data point from the sorted filter buffer at block 638.

The time of process point j is then compared to a preset precipitation time limit at block 640. Noise found in the signal at or before the preset precipitation time limit is not used in the determination of the quality of the signal. Illustratively, the precipitation time limit value is set at 10 seconds. Therefore, the integer value 40 (10 sec.×4 samples per second) is stored in key 119. If the time of process point j is less than the precipitation time limit, μC 284 increments process point j at block 626. If the time of process point j is greater than the precipitation time limit, μC 284 compares the replaced value of process point j to a noise threshold value at block 642. Illustratively, the noise threshold value is 149.9 mV. If the absolute magnitude of the filtered data point is above the preset noise threshold value, then the data is considered to be a significant noise point.

If the absolute voltage magnitude of process point j is less than the preset noise threshold value at block 642, μC 284 determines that the noise point is not significant, proceeds to block 626, and increments process point j. If the absolute magnitude of the process point j is greater than the noise threshold value at block 642, μC 284 increments a noise counter at block 644. μC 284 then compares the noise counter value to a preset noise limit value at block 645. Illustratively, the noise limit value has a value of 10 for each pass over the entire envelope. If the actual count of significant noise points is less than or equal to the noise limit value, μC 284 advances to block 626 and increments process point j. If the actual count of significant noise points is greater than the noise limit, μC 284 exits the main processing program and generates an error signal at block 504.

Figure 25A:
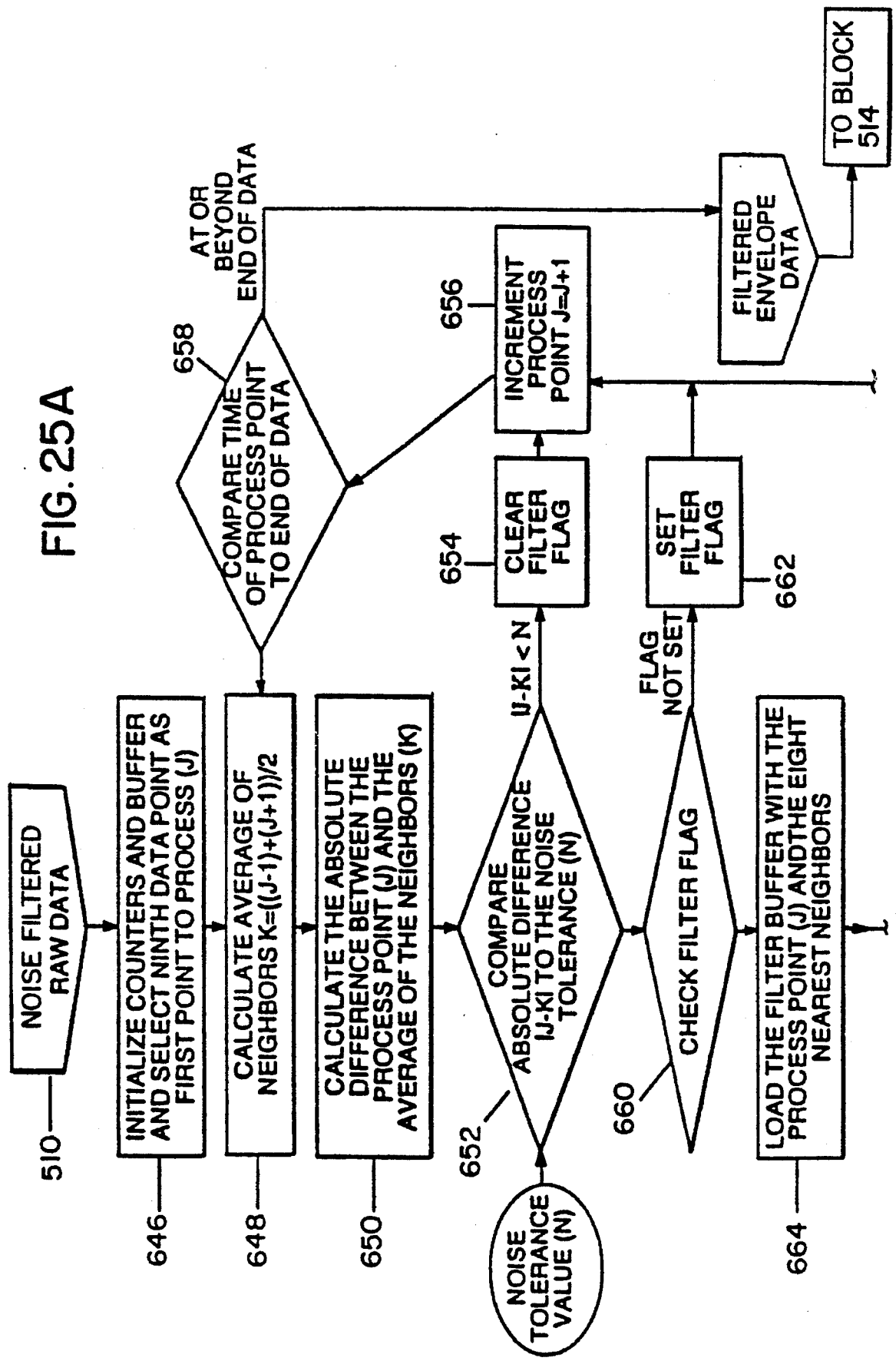
Figure 25B:
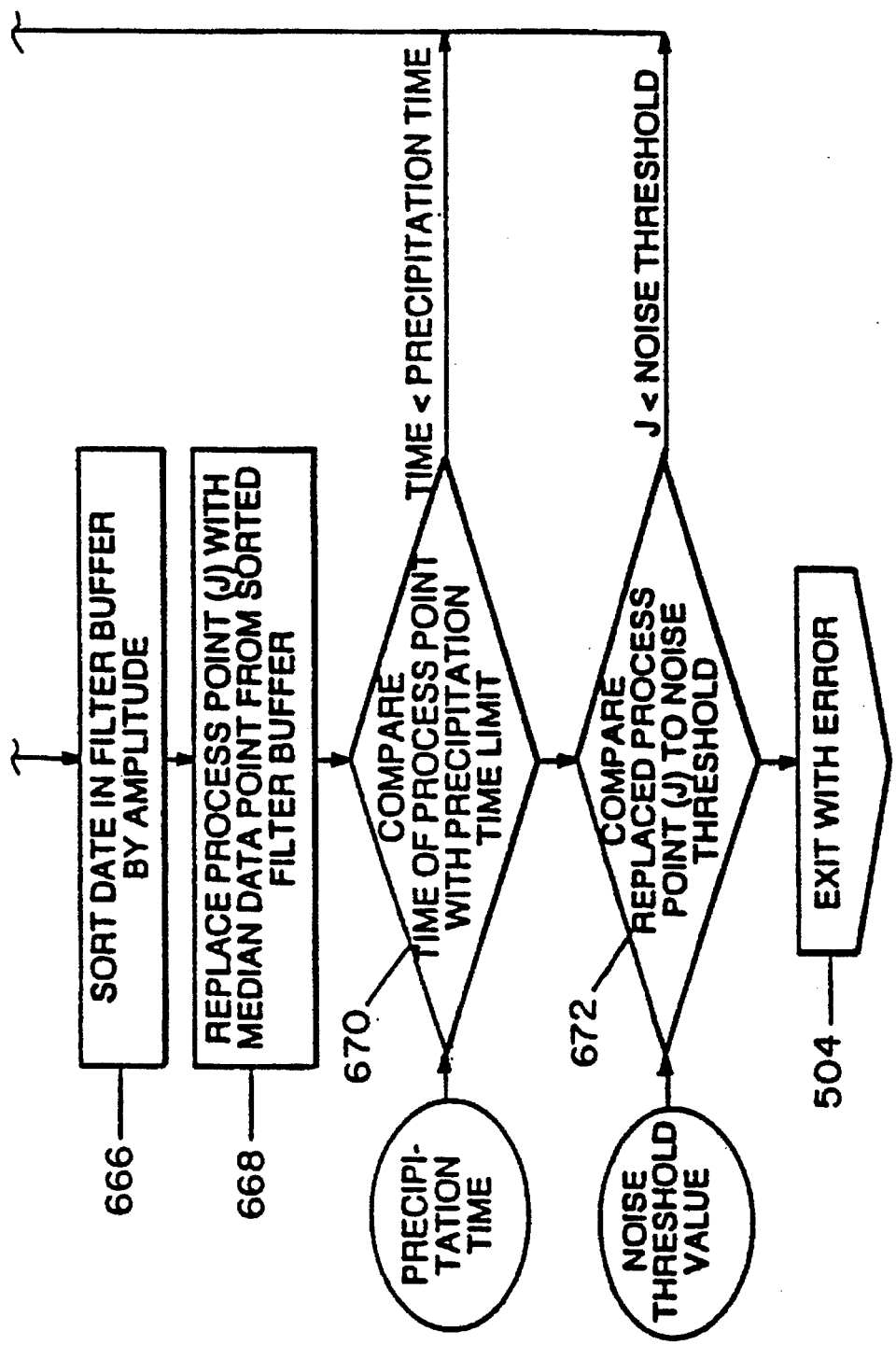

FIG. 25 is an expanded flow chart illustrating the steps performed by μC 284 at block 512. μC 284 first initializes counters and the storage buffer and selects the ninth stored data point as the first process point j as illustrated at block 646. μC 284 then calculates the average value k of the two nearest neighbors of process point j using the equation k=(value at point (j−1)+value at point (j+1))/2 as illustrated at block 648. Next, μC 284 calculates the absolute difference between the process point j and the average k of its neighbors at block 650. μC 284 then compares the calculated absolute difference to a preset noise tolerance percentage value n as illustrated at block 652. The noise tolerance percentage value n is 26. Therefore, the noise tolerance percentage is 10.156% (0.3906% ×26). A filter flag is set if the difference between the process point j and the average k of the neighbors is greater than the noise tolerance percentage value n.

If the absolute difference calculated at block 650 is less than the noise tolerance percentage value n, μC 284 clears the filter flag as illustrated at block 654. µC 284 then increments process point j by setting j=j+1 as illustrated at block 656. µC 284 then compares the time of the process point j to the end of data location as illustrated at block 658. If the new process point j is at or beyond the storage location of the end of the stored data, µC 284 proceeds to block 514 of FIG. 20. If the process point is not at or beyond the end of the data, µC 284 returns to block 648 to calculate the average value of the neighbors for the new process point j.

If the absolute difference calculated at block 650 is greater than the preset noise tolerance percentage value, µC 284 checks the filter flag at block 660. If the filter flag is not set, this indicates that the noise is caused by a process point (j+1) affecting the average k. Therefore, µC 284 does not filter the present process point j. µC 284 sets the filter flag at block 662 and then proceeds to increment process point j at block 656.

If the filter flag is set at block 660, µC 284 determines that the current process point j is a noise point since it affected the average for the preceding process point (j−1) and caused the filter flag to be set in the preceding pass of the filter. Therefore, µC 284 filters the detected noise process point j only when the filter flag is already set.

In order to filter process point j, µC 284 loads the filter buffer with process point j and its eight nearest neighbors (j−4), (j−3), (j−2), (j−1), (j+1), (j+2), (j+3), and (j+4) as illustrated at block 664. Data stored in the filter buffer is then sorted by amplitude as illustrated at block 666. Process point j is then replaced with the median data point from the sorted filter buffer at block 668.

The time of process point j is then compared to a preset precipitation time limit at block 670. The precipitation time limit is illustratively set at 10 seconds. If the time of process point j is less than the precipitation time limit, µC 284 increments process point j at block 656. If the time of process point j is greater than the precipitation time limit, µC 284 compares the replaced value of process point j to a noise threshold value at block 672. Illustratively, the noise threshold value is 149.9 mV.

If the absolute voltage magnitude of process point j is less than the preset noise threshold value at block 672, µC 284 determines that the noise point is not significant, proceeds to block 656, and increments process point j. If the absolute magnitude of the process point is greater than the noise threshold value at block 672, µC 284 exits the main processing program and generates an error signal at block 504.

Figure 26A:
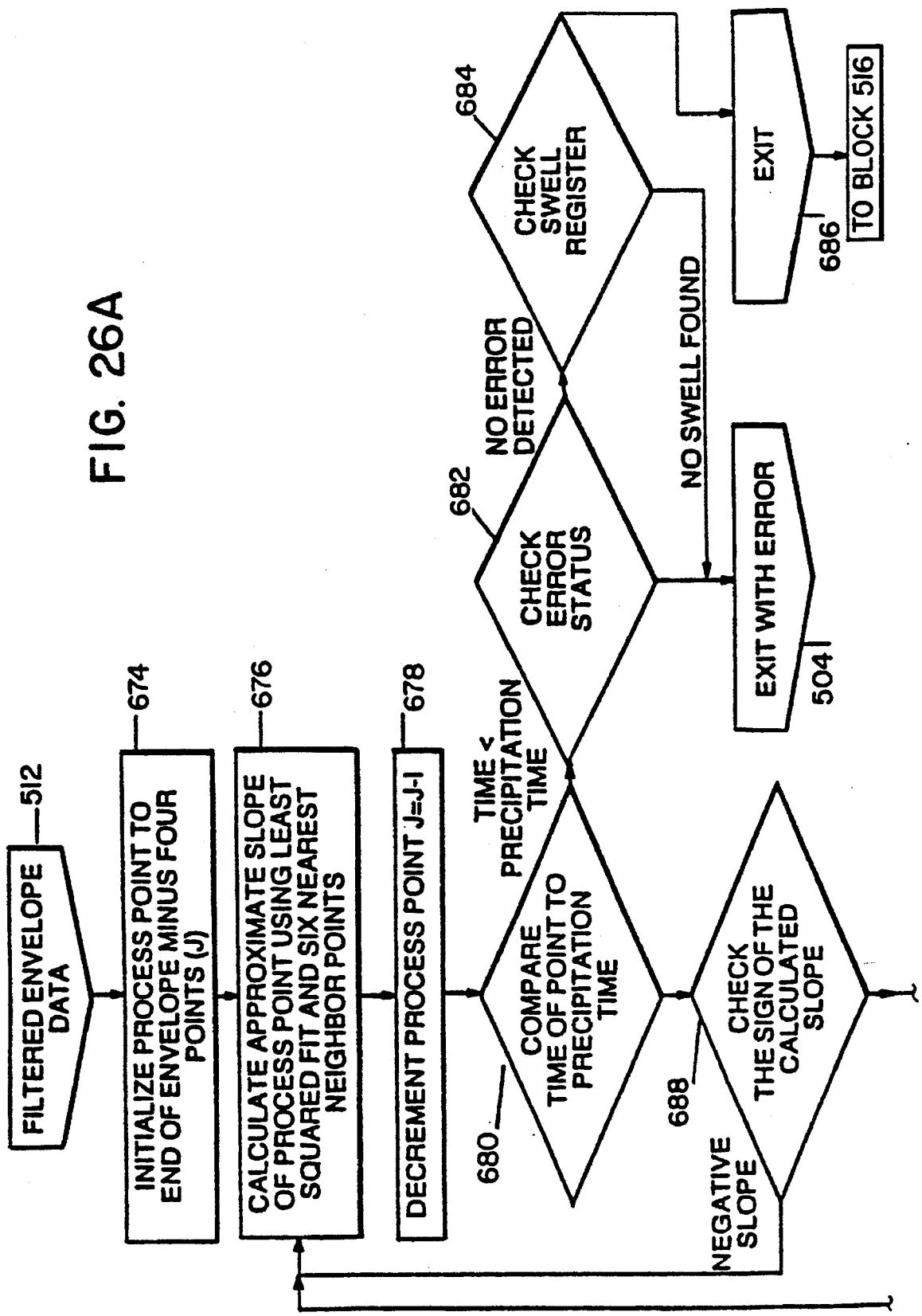
Figure 26B:
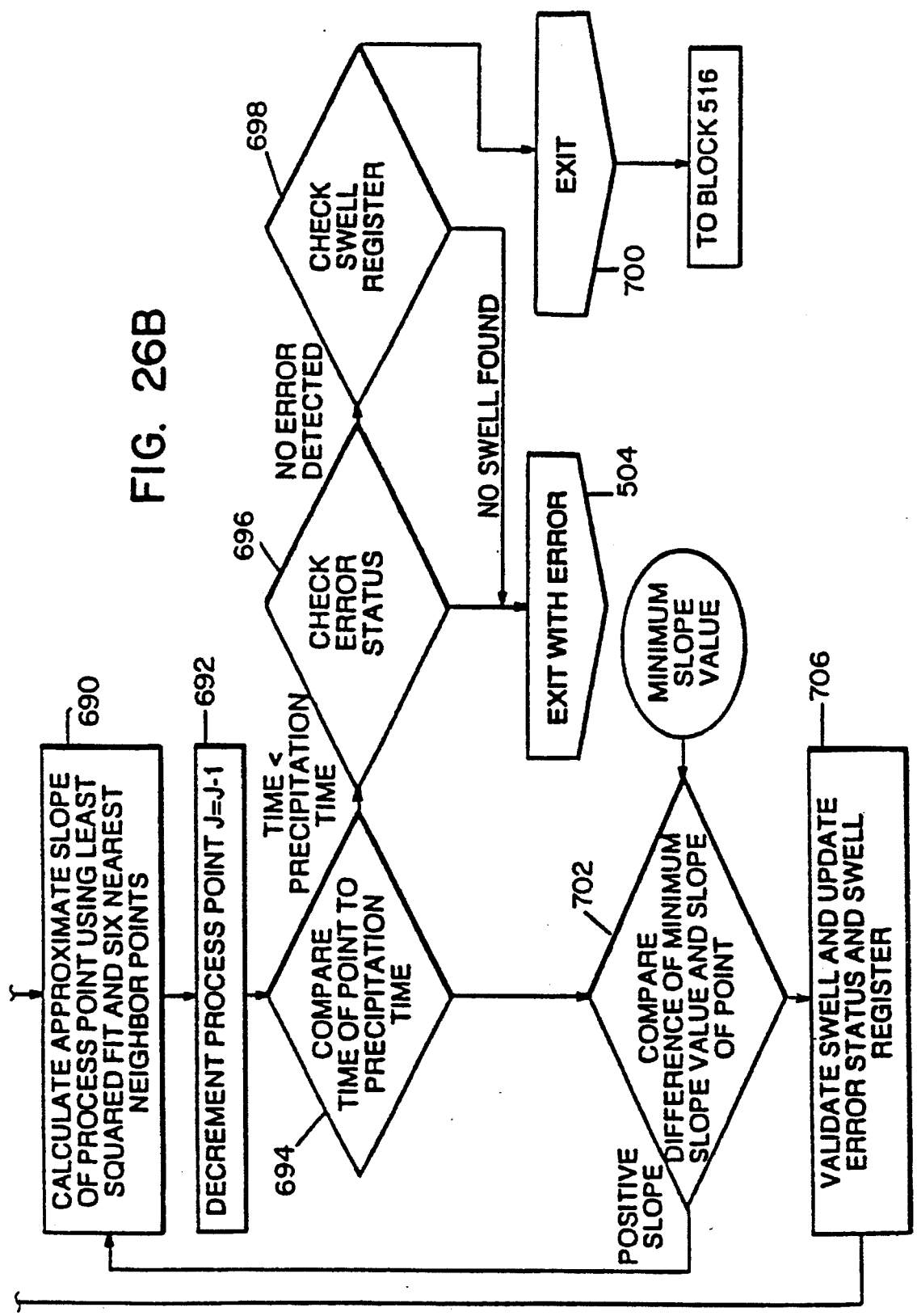

FIG. 26 illustrates the steps performed by µC 284 to determine the point in the envelope where the largest swell occurred. A swell occurs when the slope of the envelop changes from a negative slope to a positive slope. It must be remembered that the program is operating on the process points in a last in-first out manner, that is, backwards. µC 284 first initializes process point j to the end of the envelope minus four points as illustrated at block 674. In other words, µC 284 processes the envelope data in reverse order to determine the largest swell. µC 284 then calculates the approximate slope of the process point j using a least squares fit and the six nearest neighbor points (j+3), (j+2), (j+1), (j−1), (j−2), and (j−3) as illustrated at block 676. µC 284 then decreases the process point j by one at block 678 and compares the time of the process point to the precipitation time at block 680. Precipitation time is illustratively 10 seconds. Since µC 284 process as the data in reverse order, all the relevant data will be processed to look for swells before the precipitation time is reached. If the time of process point j is less than the precipitation time, µC 284 checks the error status at block 682. If no error is detected, µC 284 checks the swell register at block 684. If a swell is founds µC 284 exits at block 686 and the swell in the swell register is considered to be the largest swell. If an error is detected at block 682, µC 284 exits the main processing program and generates an error signal at block 504. If no swell is found at block 684, µC 284 exits the main processing program and generates an error signal at block 504.

If the time of process point j is greater than the precipitation time at block 680, µC 284 checks the sign of the calculated slope at block 688. If the slope is negative, µC 284 returns to block 676 and recalculates the slope of the new process point. If the slope is positive at block 688, µC 284 calculates the approximate slope of the new process point j using least squares fit and six nearest neighbors (j+3), (j+2), (j+1), (j−1), (j−2), (j−3) as illustrated at block 690. µC 284 then decreases process point j by one at block 692 and compares the time of the new process point j to the precipitation time at block 694. If the time of process point j is less than the precipitation time, µC 284 checks the error status at block 696. If no error is detected, µC 284 checks the swell register at block 698. If a swell is found, µC 284 exits at block 700 and the swell in the swell register is considered to be the largest swell. If an error is detected at block 696, µC 284 exits the main processing program and generates an error signal at block 504. If no swell is found at block 698, µC 284 exits the main processing program and generates an error signal at block 504.

If the time of process point j is greater than the precipitation time at block 694, µC 284 compares the difference of the minimum slope value and the slope at the process point at block 702. The minimum slope value is illustratively 3.9 volts/sec and establishes the minimum slope value for a swell to be considered the largest swell of the signal. The minimum swell time illustratively is set at 10 seconds. The maximum swell time illustratively is 55 seconds. µC 284 checks to determine whether the swell occurred at a location between the minimum and maximum swell times. µC 284 also checks the sign of the calculated slope at block 702. If a positive slope exists, µC 284 returns to block 690. If a negative slope exists, µC 284 validates the swell and updates the error status and swell register at block 706. When a swell is located, it must have a minimum amplitude at least equal to 250 mV. µC 284 processes the entire envelope signal and compares each detected swell to all the other detected swells if more than one swell exists. If the swells are outside minimum slope or amplitude ranges, or outside the minimum or maximum swell times, a flag is set to indicate an error. If any error flags are set, an error signal is generated. If no error flags are set, µC 284 assumes that the detected swell met the applicable conditions and is acceptable as the largest swell.

Figure 27:
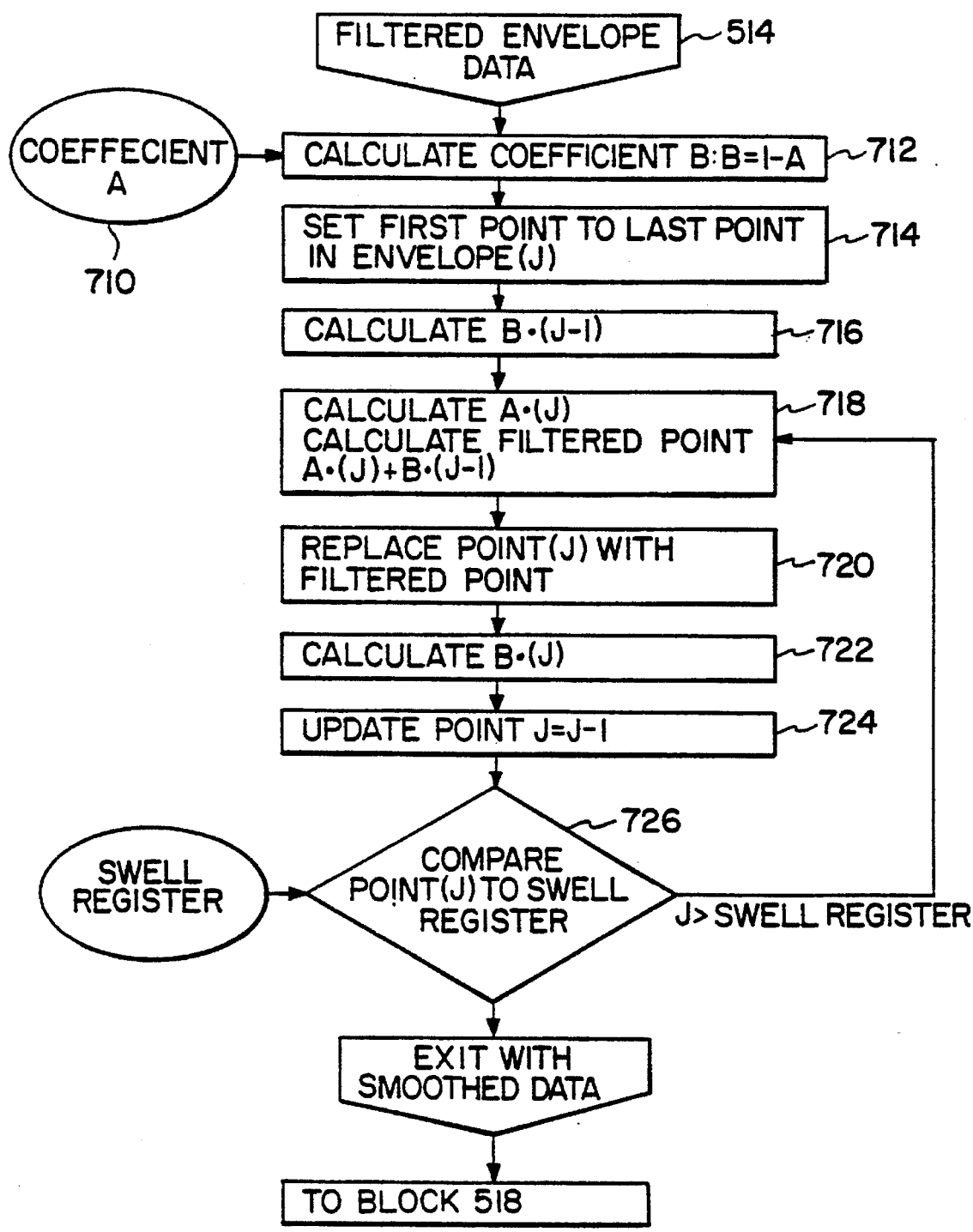

After the largest swell is detected at block 514, µC 284 smooths the signal using a recursive filter at block 516 as illustrated in detail in FIG. 27. The recursive filter uses two coefficients, A and B, to filter the swell. Coefficient A is set in key 119, illustratively at a value of 100. Coefficient A is stored in key 119 as an integer ranging from 1 to 255. Therefore, coefficient A has a value of 0.390625 (100÷256). Coefficient A is illustrated at block 710. µC 284 then calculates the value of coefficient B by setting coefficient B=1−coefficient A as illustrated at block 712. Therefore, coefficient B has a value of 0.609375. µC 284 then sets the first process point j to the last point in the envelope at block 714. µC 284 then multiplies coefficient B times process point (j−1) as illustrated at block 716. Next, µC 284 multiplies coefficient A times process point j, and then calculates the new filter point by setting j=A·(j)+B·(j−1) as illustrated at block 718. µC 284 then replaces the process point j with the filtered process point calculated at block 718 as illustrated at block 720. Next, µC 284 multiplies coefficient B times the process point j at block 722 to use in the next pass of the recursive filter, and updates process point j by setting j=j−1 at block 724. µC 284 then compares process point j to the largest swell register at block 728. If process point j is greater than the point at the leading end of the swell register, µC 284 returns to block 718. If process point j is less than the point at the leading end of the swell register, µC 284 has smoothed the entire swell and proceeds to block 518 in FIG. 20.

Figure 28A:
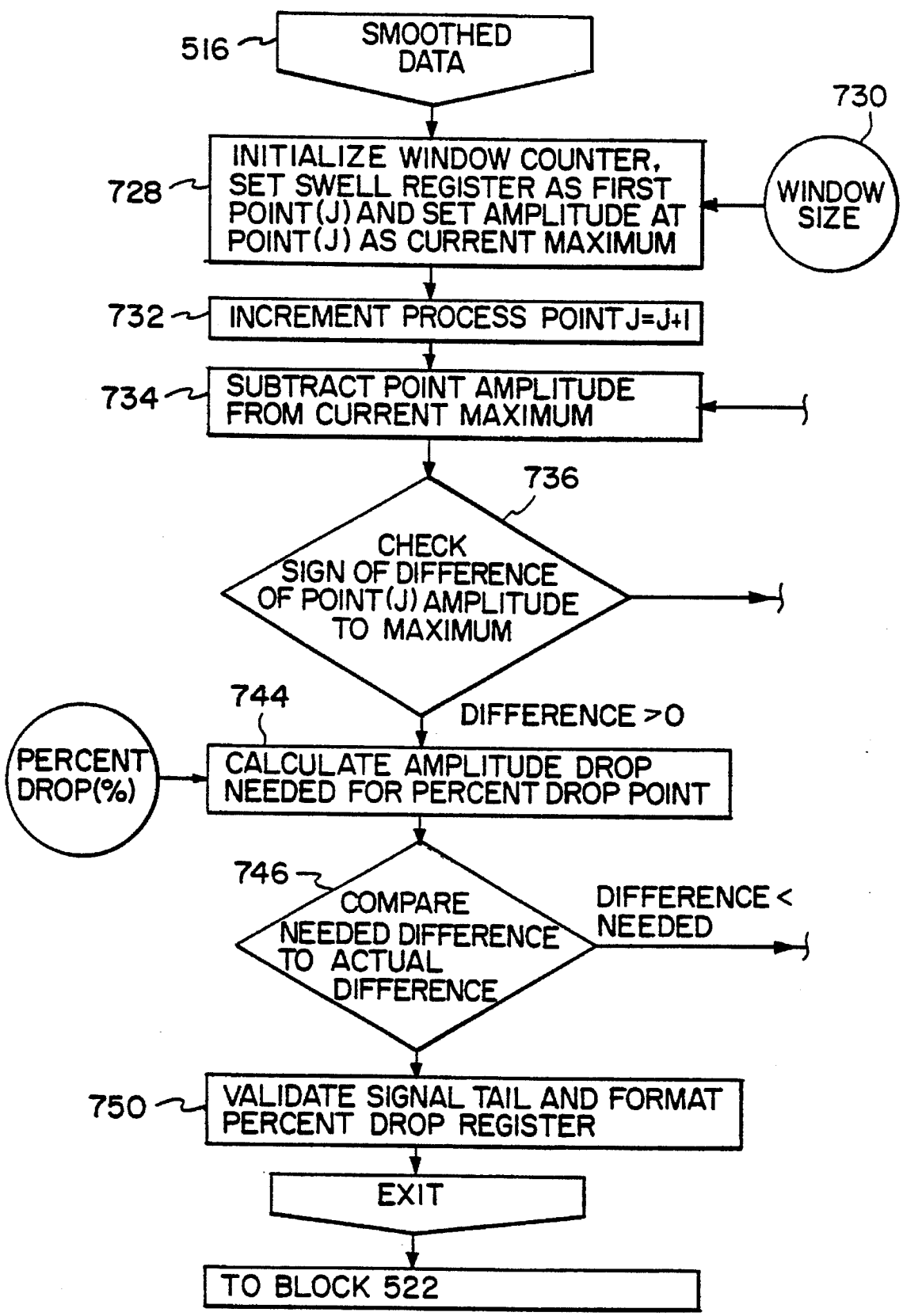
Figure 28B:
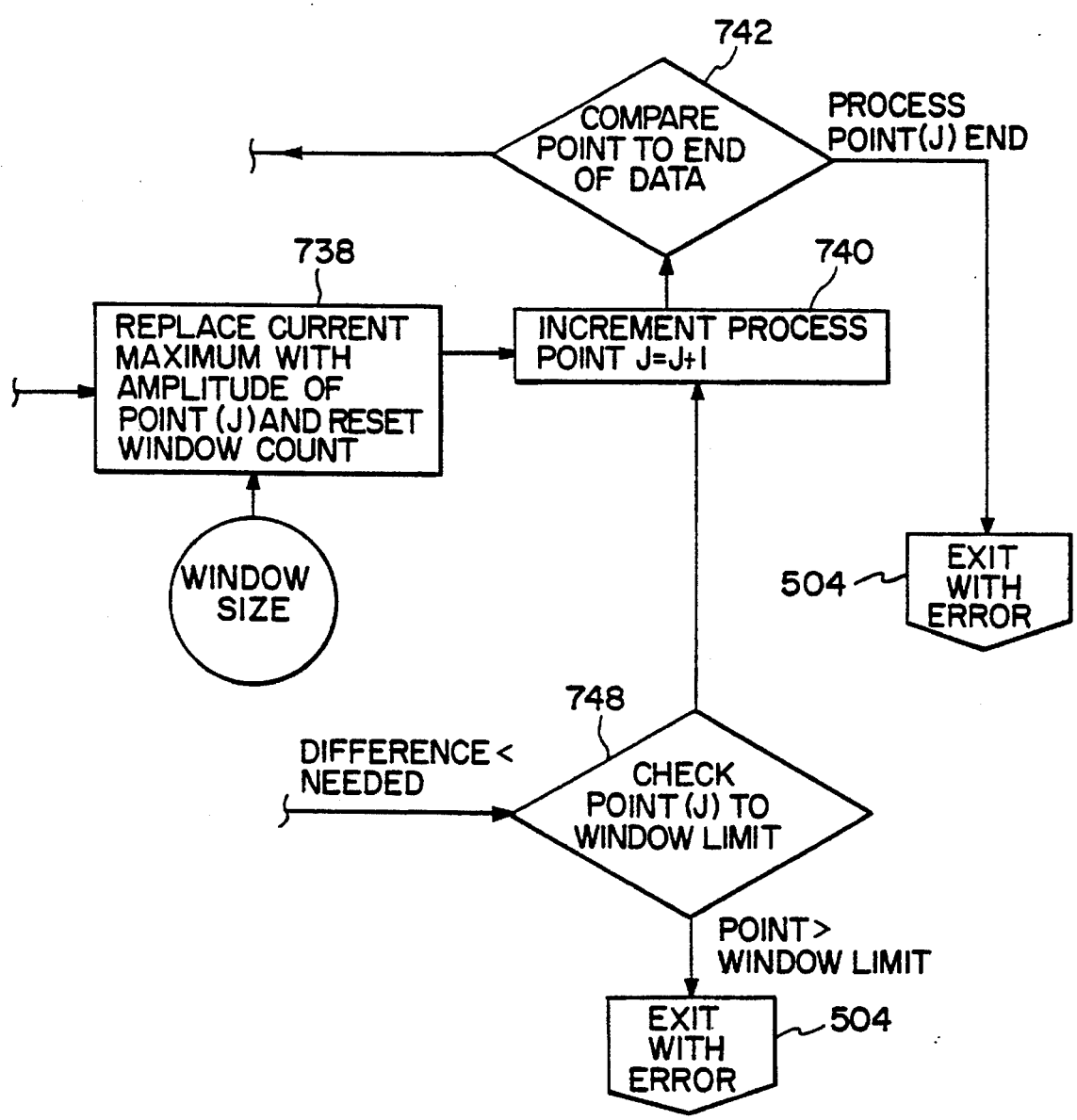

FIG. 28 illustrates the steps performed by µC 284 in blocks 518 and 520 of FIG. 20. After the swell register data is smoothed by recursive filter at block 516, µC 284 initializes a window counter illustrated at block 730, sets the swell register as the first process point j, and sets the amplitude of process point j as the current maximum value as illustrated at block 728. The window size at block 730 is set at 20 seconds from the maximum value. The preselected percentage voltage amplitude drop must occur within this window after the maximum value in order to be a valid reading. µC 284 increments process point j by one at block 732, and then subtracts the new process point j amplitude from the current maximum value from block 734. µC 284 checks the sign of the value obtained at block 734 at block 736. A negative value indicates that the new process point is larger than the stored maximum value. Therefore, if the difference at block 736 is less than zero, µC 284 replaces the current stored maximum value with the amplitude of the new process point j and resets the window count as illustrated at block 738 based on the time of the new maximum value at process point j. µC 284 then increments process point j by one at block 740, and compares the new process point to the end of data at block 742. If the process point j is greater than the end of the data, µC 284 exits the main processing program and generates an error signal at block 504. If process point j is less than the end of the data, µC 284 returns to block 734.

If the difference calculated at block 734 is greater than zero, µC 284 calculates the required amplitude drop from the stored maximum value to reach the IPT based on the preset required percentage drop at block 744. The preset percentage drop at block 745 is stored in key 119 as an integer value between 1 and 255. The percentage drop is stored as integer 13. Therefore, the illustrated percent drop is about 5.078% ((100%÷256)×13) from the maximum value. µC 284 compares the actual difference between the maximum value and the current process point j to the IPT percent drop value at block 746. If the actual difference is less than the required difference for the IPT, µC 284 compares process point j to the window limit at block 748. If the current process point j exceeds the window limit, µC 284 exits from the main processing program and generates an error signal at block 504. If the process point is less than the window limit, µC 284 returns to block 740. If the difference detected at block 746 is greater than or equal to the required difference needed for the preset percent drop, µC 284 validates the signal tail and formats the percent drop register at block 750. In block 750, µC 284 changes the units for the IPT internally to convert the value into a true time value. Specifically, µC 284 divides the address by eight and then adds the offset time to the value to obtain the true time value for the IPT corresponding to the time of the particular process point j which is 5.078% less than the maximum value in the swell. µC 284 also validates the signal tail. Using a four point average, µC 284 must verify that the tail has dropped below the maximum value by a predetermined percentage. The signal tail must have a voltage drop of at least 25% below the maximum voltage of the swell. If the tail voltage does not drop at least 25%, an error signal is generated.

µC 284 then returns to block 522 in FIG. 20 and converts the IPT time value to clinical units. For instance, µC 284 can convert the IPT to NAS, INR, Percent Quick, or PT Ratio by linear interpolation between tabulated values stored in key 119.

Although the invention has been described in detail with reference to a certain illustrated embodiment, variations and modifications exist within the scope and spirit of the invention as described and defined in the following claims.

What is claimed is:

1. A method for calculating a coagulation characteristic of a sample of blood, a blood fraction, or a control, the method comprising the steps of:

generating an output signal indicative of coagulation of the sample;

sampling the output signal at a sampling rate for a predetermined time interval to provide a plurality of sampled signal values;

storing the sampled signal values;

determining an envelope from the stored signal values;

storing the envelope; and calculating the coagulation characteristic from the stored envelope based on the maximum signal value.

2. The method of claim 1 wherein the step of calculating the coagulation characteristic includes the steps of examining the stored envelope to locate a maximum value of the stored envelope and identifying a stored value in the envelope which is a predetermined percentage less than said maximum value, said coagulation characteristic being related to the number of stored samples between the beginning of the sampling interval and the thus-identified stored value.

3. The method of claim 2 wherein the predetermined percentage is about 5%.

4. The method of claim 2, further comprising the step of converting the number of stored samples between the beginning of the sampling interval and the thus-identified stored value into clinical units corresponding to the coagulation characteristic.

5. The method of claim 1, further comprising the step of filtering the stored sampled signal values to provide filtered stored sampled signal values before the step of calculating the envelope.

6. The method of claim 1, further comprising the step of filtering the stored envelope before the step of calculating the coagulation characteristic.

7. The method of claim 6 wherein the filtering step includes the steps of selecting a process point from among the stored sampled signal values, the process point having two nearest neighbor sampled signal values, calculating an average value of the two nearest neighbor sampled signal values, forming an absolute difference between the average value and the process point, establishing a noise tolerance value, comparing the absolute difference to the noise tolerance value, clearing a filter flag if the absolute difference is less than the noise tolerance value, checking the filter flag to determine if the filter flag is set if the absolute difference is greater than the noise tolerance value, forming a filtered signal value, replacing the process point with the filtered signal value only if the filter flag is set during the checking step, setting the filter flag if the filter flag is not set, and repeating the method with the next stored sampled signal value.

8. The method of claim 7 wherein the forming and replacing steps comprise the steps of forming a median sampled signal value from a plurality of stored sampled signal values neighboring the process point, and replacing the process point with the median sampled signal value.

9. The method of claim 7, further comprising the steps of establishing a noise threshold value, comparing the filtered signal value to the noise threshold value after the replacing step, providing a noise counter for storing a noise value, incrementing the noise value if the filtered signal value is greater than the noise threshold value, establishing a noise limit, comparing the noise value to the noise limit, and generating an error signal if the noise value is greater than the noise limit.

10. The method of claim 9, further comprising the steps of establishing a minimum time limit, establishing a time of the process point, comparing the time of the process point with the minimum time limit before the step of comparing the filtered signal value to the noise threshold value, and advancing to the repeating step if the time of the process point is less than the minimum time limit.

11. The method of claim 6 wherein the filtering step includes the steps of selecting a process point from among the stored sampled signal values, the process point having two nearest neighbor sampled signal values, calculating an average value of the two nearest neighbor sampled signal values, forming an absolute difference between the average value and the process point, establishing a noise tolerance value, comparing the absolute difference to the noise tolerance value to determine whether noise is present either at the process point or at one of the two nearest neighbor sampled signal values, determining whether the noise is at the process point or at one of the two nearest neighbor sampled signal values if the absolute difference is greater than the noise tolerance value, forming a filtered signal value, and replacing the process point with the filtered signal value only if the noise is located at the process point.

12. The method of claim 1, further comprising the step of recursively filtering the stored envelope for smoothing the stored envelope before the step of calculating the coagulation characteristic.

13. The method of claim 1, further comprising the step of examining stored envelope values in reverse time order to determine a slope of the envelope at each of the stored envelope values, identifying all relative maxima in the stored envelope values, determining a range of stored envelope values corresponding to each relative maximum, and comparing the identified relative maxima to identify an absolute maximum in the stored envelope values.

14. The method of claim 13, wherein the step of calculating the coagulation characteristic comprises the step of calculating the coagulation characteristic from the stored signal values within the determined range of envelope values corresponding to the identified absolute maximum.

15. The method of claim 13, further comprising the steps of establishing a minimum amplitude value, comparing each identified relative maximum to the minimum amplitude value, and disregarding each identified relative maximum having a value less than the minimum amplitude value.

16. The method of claim 13, further comprising the steps of establishing a minimum slope value, comparing the slope of the envelope at each identified relative maximum to the minimum slope value, and disregarding each identified relative maximum at which the slope is less than the minimum slope value.

17. The method of claim 13 wherein the step of identifying all relative maxima in the stored envelope values includes the steps of monitoring the slope at each of the stored envelope values to detect a change in slope from a negative slope to a positive slope, thereby indicating that a relative maximum has occurred in the stored envelope values.

18. The method of claim 13, further comprising the steps of establishing minimum and maximum time limits, determining a time at which each identified relative maximum occurred, comparing the time of each identified relative maximum to the minimum and maximum time limits, and disregarding each identified relative maximum which occurred before the minimum time limit or after the maximum time limit.

19. The method of claim 1, further comprising the steps of establishing positive and negative limits, comparing the sampled signal values to the positive and negative limits, and generating an error signal upon detection of a sampled signal value greater than the positive limit or less than the negative limit.

20. A method for calculating a coagulation characteristic of a sample of blood, a blood fraction, or a control, the method comprising the steps of:

generating an output signal indicative of coagulation of the sample;

sampling the output signal at a sampling rate for a predetermined time interval to provide a plurality of sampled signal values;

storing the sampled signal values;

determining an envelope from the stored signal values;

storing the envelope; and calculating the coagulation characteristic from the stored envelope by locating a maximum value of the stored envelope; and identifying a stored value in the envelope which is a predetermined percentage less than said maximum value, said coagulation characteristic being related to the number of stored samples between the beginning of the sampling interval and the thus-identified stored value.

21. The method of claim 20 wherein the predetermined percentage is about 5%.

22. The method of claim 20, further comprising the step of converting the number of stored samples between the beginning of the sampling interval and the thus-identified signal value into clinical units corresponding to the coagulation characteristic.

23. The method of claim 20, further comprising the step of filtering the stored sampled signal values to provide filtered stored sampled signal values after the step of storing the sample signal values and before the determining step.

24. The method of claim 20, further comprising the step of filtering the stored envelope before the locating step.

25. The method of claim 20, further comprising the step of recursively filtering the stored envelope for smoothing the stored envelope before the locating step.

26. A method for calculating a coagulation characteristic of a sample of blood, a blood fraction, or a control, the method comprising the steps of:

generating an output signal indicative of coagulation of the sample;

sampling the output signal at a sampling rate for a predetermined time interval to provide a plurality of sampled signal values;

storing the sampled signal values;

rectifying the stored sampled signal values to provide a plurality of envelope values;

storing the envelope values;

examining the stored envelope values in reverse time order to determine a slope of the envelope at each of the stored envelope values;

identifying all relative maxima in the stored envelope values and determining a range of stored envelope values corresponding to each relative maximum;

comparing the identified relative maxima to locate an absolute maximum in the stored envelope values; and calculating the coagulation characteristic from the stored envelope values within the determined range of envelope values corresponding to the absolute maximum.

27. The method of claim 26, wherein the step of calculating the coagulation characteristic includes the steps of locating an absolute maximum signal value within the absolute maximum range and identifying a stored signal value which is a predetermined percentage less than said absolute maximum signal value, said coagulation characteristic being related to the number of stored samples between the beginning of the sampling interval and the thus-identified stored signal value.

28. The method of claim 27 wherein the predetermined percentage is about 5%.

29. The method of claim 27, further comprising the step of converting the number of stored samples between the beginning of the sampling interval and the thus-identified stored signal value into clinical units corresponding to the coagulation characteristic.

30. The method of claim 26, further comprising the step of filtering the stored signal values to provide filtered stored signal values before the rectifying step.

31. The method of claim 26, further comprising the step of filtering the stored envelope values before the examining step.

32. The method of claim 26, further comprising the step of recursively filtering the stored envelope values for smoothing the stored envelope after the comparing step.

33. An apparatus for calculating a coagulation characteristic of a sample of blood, a blood fraction, or a control, the apparatus comprising means for generating an output signal indicative of coagulation of the sample, and means for sampling the output signal at a sampling rate for a predetermined time interval to provide a plurality of sampled signal values, for storing the sampled signal values, for determining an envelope from the stored signal values, for storing the envelope, and for calculating the coagulation characteristic from the stored envelope based on the maximum signal value.

34. The apparatus of claim 33, wherein the means for calculating the coagulation characteristic also examines the stored envelope to locate a maximum value of the stored envelope and identifies a stored value in the envelope which is a predetermined percentage less than said maximum value, said coagulation characteristic being related to the number of stored samples between the beginning of the sampling interval and the thus-identified stored value.

35. The apparatus of claim 34 wherein the predetermined percentage is about 5%.

36. The apparatus of claim 35 wherein the means for sampling the output signal further comprises means for converting the number of stored samples between the beginning of the sampling interval and the thus-identified stored value into clinical units corresponding to the coagulation characteristic.

37. The apparatus of claim 33 wherein the means for sampling the output signal further comprises means for filtering the stored sampled signal values to provide filtered stored sampled signal values.

38. The apparatus of claim 33 wherein the means for sampling the output signal further comprises means for filtering the stored envelope 39. The apparatus of claim 33 wherein the means for sampling the output signal further comprises means for recursively filtering the stored envelope.

40. The apparatus of claim 33 wherein the means for sampling the output signal further comprises means for examining stored envelope values in reverse time order to determine a slope of the envelope at each of the stored envelope values, for identifying all relative maxima in the stored envelope values, for determining a range of stored envelope values corresponding to each relative maximum, and for comparing the identified relative maxima to identify an absolute maximum in the stored envelope values.

41. An apparatus for calculating a coagulation characteristic of a sample of blood, a blood fraction, or a control, the apparatus comprising means for generating an output signal indicative of coagulation of the sample, means for sampling the output signal at a sampling rate for a predetermined time interval to provide a plurality of sampled signal values, for storing the sampled signal values, for determining an envelope from the stored signal values, for storing the envelope, for calculating the coagulation characteristic from the stored envelope by identifying a maximum value from the stored envelope and for identifying a stored envelope value which is a predetermined percentage less than said maximum value, said coagulation characteristic being related to the number of stored samples between the beginning of the sampling interval and the thus-identified stored envelope value.

42. The apparatus of claim 41 wherein the predetermined percentage is about 5%.

43. The apparatus of claim 41 wherein the means for sampling the output signal further comprises means for converting the number of stored samples between the beginning of the sampling interval and the thus-identified envelope signal value into clinical units corresponding to the coagulation characteristic.

44. The apparatus of claim 41 wherein the means for sampling the output signal further comprises means for filtering the stored sampled signal values to provide filtered stored sampled signal values.

45. The apparatus of claim 41 wherein the means for sampling the output signal further comprises means for filtering the stored envelope.

46. The apparatus of claim 41 wherein the means for sampling the output signal further comprises means for recursively filtering the stored envelope.

47. An apparatus for calculating a coagulation characteristic of a sample of blood, a blood fraction, or a control, the apparatus comprising means for generating an output signal indicative of coagulation of the sample, means for sampling the output signal at a sampling rate for a predetermined time interval to provide a plurality of sampled signal values, for storing the sampled signal values, for rectifying the stored sampled signal values to provide a plurality of envelope values, for storing the envelope values, for examining the stored envelope values in reverse time order to determine a slope of the envelope at each of the stored envelope values, for identifying all relative maxima in the stored envelope values, for determining a range of stored envelope values corresponding to each relative maximum, for comparing the identified relative maxima to each other to locate an absolute maximum in the stored envelope values, and for calculating the coagulation characteristic from the stored signal values within the determined range of envelope values corresponding to the absolute maximum.

48. The apparatus of claim 47 wherein the means for sampling the output signal further includes means for locating a maximum signal value within the absolute maximum range and for identifying a stored signal value which is a predetermined percentage less than said maximum signal value, said coagulation characteristic being related to the number of stored samples between the beginning of the sampling interval and the thus-identified stored signal value.

49. The apparatus of claim 48 wherein the predetermined percentage is about 5%.

50. The apparatus of claim 48 wherein the means for sampling the output signal further comprises means for converting the number of stored samples between the beginning of the sampling interval and the thus-identified stored signal value into clinical units corresponding to the coagulation characteristic.

51. The apparatus of claim 47 wherein the means for sampling the output signal further comprises means for filtering the stored signal values.

52. The apparatus of claim 47 wherein the means for sampling the output signal further comprises means for filtering the stored envelope values.

53. The apparatus of claim 47, wherein the means for sampling the output signal further comprises means for recursively filtering the stored envelope values.

* * * * *